US008338185B2

(12) United States Patent
Lima et al.

(10) Patent No.: US 8,338,185 B2
(45) Date of Patent: Dec. 25, 2012

(54) METHODS OF DETERMINING POTENCY OF CHEMICALLY-SYNTHESIZED OLIGONUCLEOTIDES

(75) Inventors: Walter F. Lima, San Diego, CA (US); Timothy Vickers, Oceanside, CA (US); Stanley T. Crooke, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/311,366

(22) Filed: Dec. 5, 2011

(65) Prior Publication Data
US 2012/0077276 A1 Mar. 29, 2012

Related U.S. Application Data

(63) Continuation of application No. 12/445,854, filed as application No. PCT/US2007/081857 on Oct. 18, 2007, now Pat. No. 8,093,061.

(60) Provisional application No. 60/862,025, filed on Oct. 18, 2006.

(51) Int. Cl.
*G01N 33/53* (2006.01)
*G01N 33/00* (2006.01)

(52) U.S. Cl. ............... 436/86; 435/4; 435/41; 435/199; 435/91.2; 435/89

(58) Field of Classification Search ............ 436/86; 435/4, 6, 183, 195, 196, 199, 41, 84, 85, 435/89, 91.1, 91.2
See application file for complete search history.

(56) References Cited

OTHER PUBLICATIONS

Chendrimada, "TRBP recruits the Dicer complex to Ago2 for microRNA processing and gene silencing" Nature (2005) 436:740-744.

Dean et al., "Identification and Characterization of Second-Generation Antisense Oligonucleotides" Antisense Nucleic Acid Drug Dev. (1997) 7:229-233.
Doi et al., "Short-Interfering-RNA-Mediated Gene Silencing in Mammalian Cells Requires Dicer and eIF2C Translation Initiation FActors" Curr. Biol. (2003) 13:41-46.
Kanellopoulou et al., "Dicer-deficient mouse embryonic stem cells are defective in differentiation and centromeric silencing" Genes Dev. (2005) 19:489-501.
Koller et al., "Competition for RISC binding predicts in vitro potency of siRNA" Nucleic Acids Research (2006) 34(16):4467-4476.
Kraynack et al., "Small interfering RNAs containing full 2'-O-methylribonucleotide-modified sense strands display Argonaute2/eIF2C2-dependent activity" RNA (2006) 12:163-176.
Liu et al., "Argonaute2 is the Catalytic Engine of Mammalian RNAi" Science (2004) 305:1437-1441.
Murchison et al., "Characterization of Dicer-deficient murine embryonic stem cells" PNAS (2005) 102:12135-12140.
Ohrt et al., "In situ fluorescence analysis demonstrates active siRNA exclusion from the nucleus by Exportin 5" Nucleic Acids Res. (2006) 34(5):1369-1380.
Sontheimer, "Assembly and Functions of RNA Silencing Complexes" Nat. Rev. Mol. Cell Biol. (2005) 6(2):127-138.
Vickers et al., "Reduced levels of Ago2 expression result in increased siRNA competition in mammalian cells" Nucleic Acid Research (2007) 35(19):6598-6610.
Winer et al., "Development and Validation of Real-Time Quantitative Reverse Transcriptase—Polymerase Chain Reaction for Monitoring Gene Expression in Cardiac Myocytesin Vitro" Anal. Biochem. (1999) 270:41-49.
International Search Report for application No. PCT/US2007/081857 dated May 30, 2008.

*Primary Examiner* — Christine T Mui
(74) *Attorney, Agent, or Firm* — Isis Patent Department

(57) ABSTRACT

Provided herein are methods for determining potency of RNAi agents. Such methods include, but are not limited to, cell-based and cell-free assays that measure binding of an RNAi agent with Ago2 or that measure Ago2 activity in the presence of such RNAi agents. Also provided are assays that determine potency of RNAi agents by assessing their ability to compete with other RNAi agents, including control RNAi agents, for binding and/or activation of Ago2.

13 Claims, 6 Drawing Sheets

| [PTEN siRNA] | 0 nM | 2 nM | 6 nM | 20 nM |
|---|---|---|---|---|
| | Eg5 siRNA 50% Inhibitory Concentration (pM) | | | |
| HeLa | 92 ± 18 | 163 ± 27 | 343 ± 53 | 772 ± 227 |
| T47D | 76 ± 15 | 128 ± 37 | 171 ± 35 | 495 ± 114 |
| U87-MG | 198 ± 45 | 841 ± 292 | 1160 ± 293 | 4390 ± 2123 |

FIG 5A
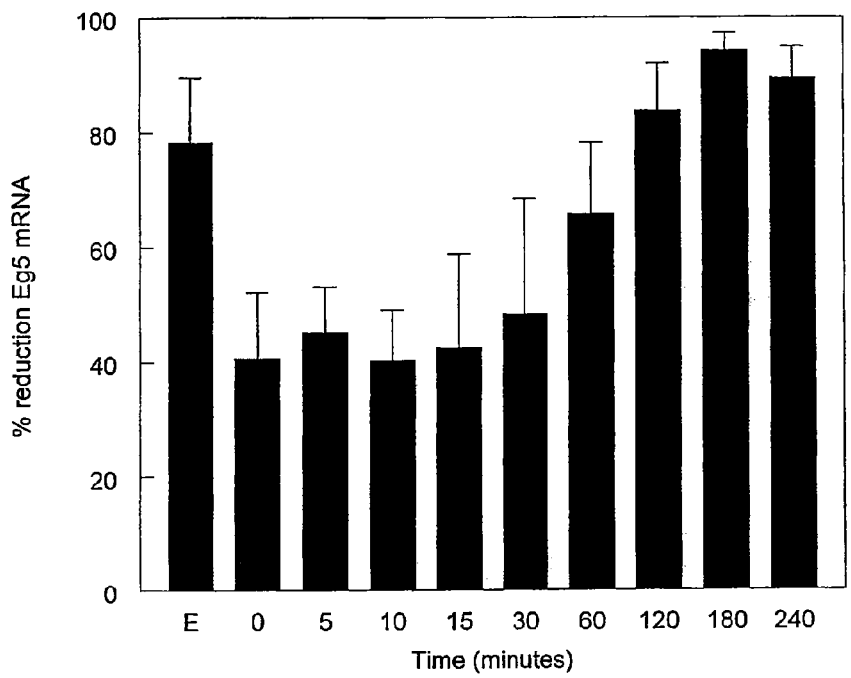
FIG 5B
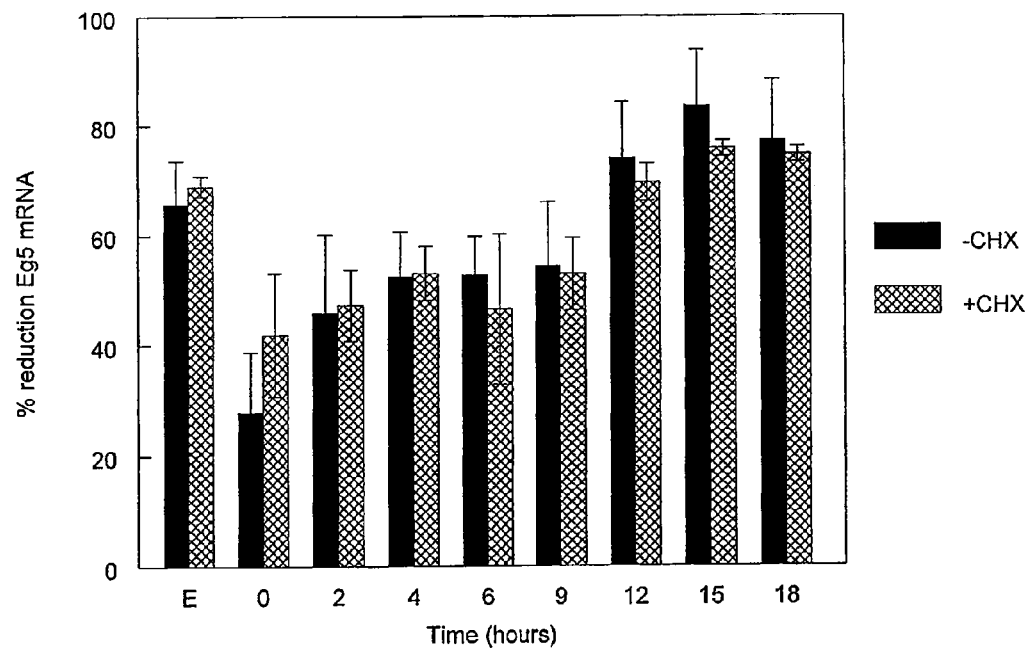
Figure 5

METHODS OF DETERMINING POTENCY OF CHEMICALLY-SYNTHESIZED OLIGONUCLEOTIDES

CROSS REFERENCE TO RELATED APPLICATIONS

This application is a continuation of U.S. application Ser. No. 12/445,854 filed Jun. 11, 2010, allowed Sep. 2, 2011, which is a U.S. National Phase filing under 35 U.S.C. 371 claiming priority to International Application No. PCT/US2007/081857, filed Oct. 18, 2007, which claims the benefit of priority under 35 U.S.C. 119(e) to U.S. Provisional Application No. 60/862,025 Oct. 18, 2006, each of which is incorporated herein by reference in its entirety.

SEQUENCE LISTING

The present application is being filed along with a Sequence Listing in electronic format. The Sequence Listing is provided as a file entitled CORE007USC1SEQ.txt, created on Dec. 2, 2011, which is 11.9 Kb in size. The information in the electronic format of the sequence listing is incorporated herein by reference in its entirety.

FIELD OF THE INVENTION

The present invention is drawn to methods of determining the potency of one or more chemically synthesized RNAi agents.

BACKGROUND OF THE INVENTION

RNA interference (RNAi) is a mechanism by which double-stranded RNA triggers the silencing of target gene expression by inducing sequence-specific target mRNA degradation. In certain instances, short interfering RNAs (siRNAs), dsRNA duplexes of 21-23 nucleotides, are mediators in the RNAi pathway that lead to degradation of specific mRNAs through the RNA induced silencing complex (RISC). Once introduced into cells, siRNA molecules bind to Argonaute2, a component of RISC, that catalyzes the cleavage of the target mRNA.

SUMMARY OF THE INVENTION

Here we show that siRNA competition, which varies significantly between cell lines, is correlated to differences in the expression levels of Ago2. While cellular Ago2 levels have dramatic effects on siRNA competition and potency, levels of other RISC-associated proteins do not. We further demonstrate the role of Ago2 in siRNA competition and potency by overexpression and siRNA mediated reduction of Ago2 within cells. In addition, we show that when Ago2 is limiting, siRNAs with higher affinity for Ago2 are favored for RISC loading due to more favorable binding affinity for purified Ago2. Finally, siRNA competition was used to analyze the kinetics of RISC loading and unloading. After transfection, RISC loading occurs in approximately 2 hours, then siRNAs remain associated with RISC for 8-12 hours, but new protein synthesis is not required to generate active RISC.

Therefore, the present invention is drawn to methods of determining the relative potency of one or more chemically synthesized RNAi agents by measuring the binding efficiencies of one or more chemically synthesized RNAi agents to human eukaryotic translation initiation factor 2C, 2 (eIF2C2) (Argonaut 2 or Ago2), Accession No. NP_036286, which is herein incorporated by reference. Potency as contemplated herein is the RNAi agent's ability to activate RISC and reduce the amount of target RNA to which the RNAi agent is designed. In an embodiment of the invention a labeled target RNA segment can be introduced into the in vitro system to measure the amount of the labeled target RNA segment is cleaved by the activated RNAi agent-activated RISC. In addition, the present invention contemplates determining the relative potency of one or more compounds in an in vitro assay comprising either recombinant human Ago2 or immunoprecipitated Ago2. The types of binding assays that could be useful in the context of the present invention would include techniques well known by those of ordinary skill in the art in determining potency as indicated by binding affinity. These techniques include, but are not limited to, homologous saturation, competition, activity (competition), gel shift, filter binding, or size-exclusion chromatography. An additional embodiment of the invention would also be the use of in silico screening of test RNAi agents to determine binding efficiency to Ago2 and therefore the test RNAi agent's potency.

The methods disclosed herein are useful in the developing a structure activity relationship for chemically-synthesized RNAi agents. In an embodiment of the invention the RNAi agents are antisense oligonucleotides which have one or more sugar-modified nucleotide, modified internucleoside linkage, or one modified nucleobase. In a certain embodiment, the sugar modified nucleotides are 2'-modified nucleotides or bicyclic nucleotides. In an additional embodiment, the modified internucleoside linkages are phosphorothioates.

BRIEF DESCRIPTION OF THE DRAWINGS

FIG. 5. Kinetics of RISC loading and unloading. A) RISC loading. HeLa cells were treated with Eg5 siRNA at 300 pM. 10 nM PTEN siRNA competitor was added between 0 and 240 minutes after the initiation of the Eg5 siRNA transfection. Transfections were carried out for a total of 5 hours. Cells were harvested the following day and total RNA purified. The percent inhibition of Eg5 mRNA is shown at the various timepoints for the addition of PTEN competitor. E=Eg5 siRNA only, no competitor. B) RISC unloading. HeLa cells were treated for 3 hours with PTEN siRNA. Cells were washed then treated with 300 pM Eg5 siRNA at 0 to 18 hours following the removal of the PTEN siRNA. Transfections were carried out for 3 hours. The following day cells were harvested and total RNA purified. The percent inhibition of Eg5 mRNA is shown at the various timepoints following removal of PTEN competitor siRNA. The experiment was performed in the presence (solid bars) or absence (striped bars) of 25 µg/ml cycloheximide (CHX).

Tables

TABLE I

Figure 1:
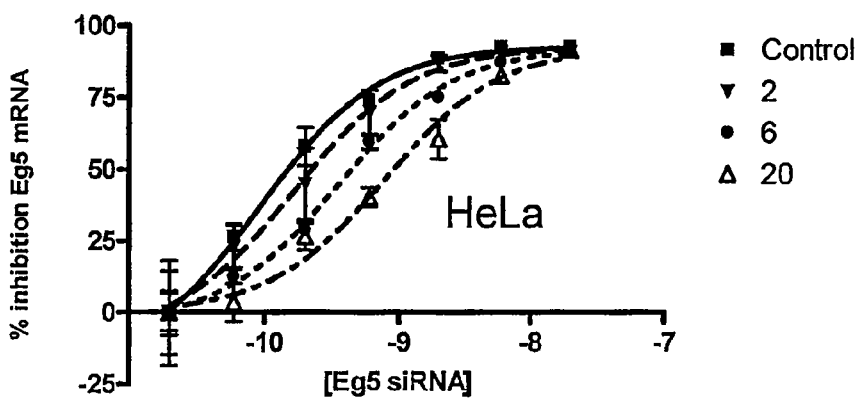
FIG. 1: Magnitude of PTEN and Eg5 siRNA competition varies between cell lines. Cells were treated at doses 0.02 to 20 nM Eg5 siRNA in the presence of PTEN competitor siRNA at a dose of 2, 6, or 20 nM for 4 hours. The following day qRT/PCR was performed to assess the reduction of Eg5 mRNA. $IC_{50}$ curves are shown for Eg5 siRNA mediated mRNA reduction in the presence of 0 (■), 2 (▼), 6 (●), or 20 (A) nM PTEN siRNA. A) HeLa cells. B) T47D cells. C) U87-MG cells. Calculated $IC_{50}$'s with standard error for each Eg5 mRNA inhibition are shown at the bottom of the figure.
Figure 1:
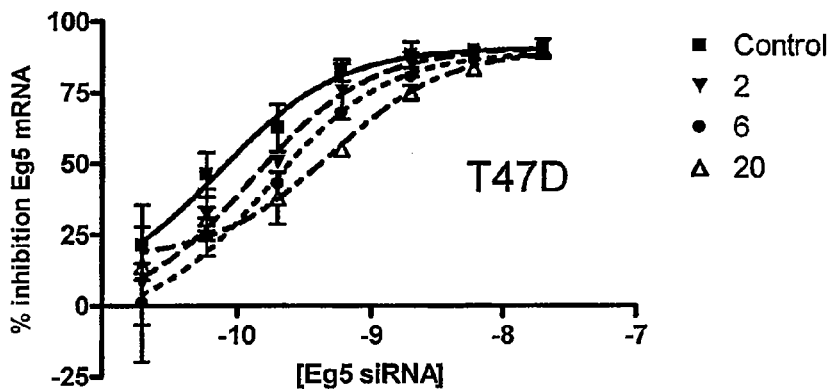
Figure 1:
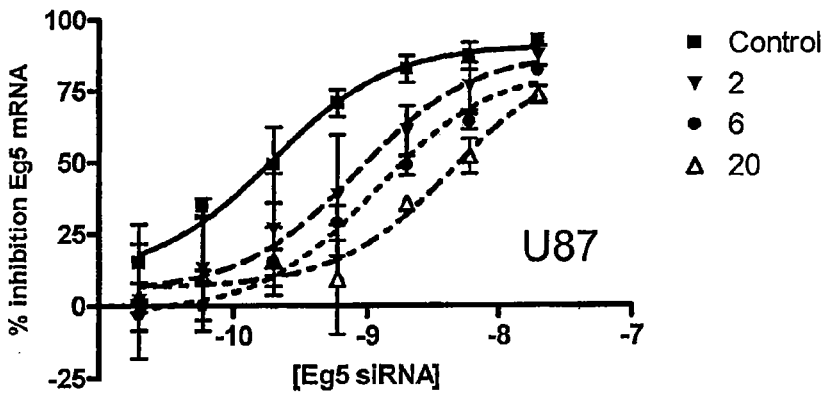

Overexpression of Ago2 in U87-MG cells affects siRNA potency and competition.

|  | Control | | Ago2 | |
| --- | --- | --- | --- | --- |
| 10 nM PTEN siRNA | − | + | − | + |
| $IC_{50}$ (pM) | 291 ± 79 | 1640 ± 499 | 65 ± 18 | 138 ± 40 |
| Fold Change $IC_{50}$ | | 5.6 | | 2.1 |

U87-MG cells were transfected with a pCMV-Ago2. After 24 hours Ago2 overexpression was confirmed by Western blot and cells were seeded in 96 well plates then treated with Eg5 siRNA at doses from 2 pM to 60 nM (N = 4/dose) in the presence or absence of 10 nM PTEN competitor siRNA for 4 hours. The following day $IC_{50}$s for Eg5 mRNA reduction were generated by qRT/PCR. Calculated $IC_{50}$'s with standard error for control and Ago2 overexpressing cells, along with the fold change in $IC_{50}$ in the presence of competitor are shown.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989; which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "Ago2" refers to a protein having Accession No. NP_036286 and variants thereof.

As used herein, the term "binding affinity" refers to the association between two molecules. Binding is typically expressed as $K_d$. In certain embodiments, binding affinity refers to the association of an RNAi agent with Ago2.

As used herein, the term "Ago2 binding affinity" refers to the binding affinity of a molecule with Ago2.

As used herein, the term "RNAi" refers to modulation of a target nucleic acid or target protein through RISC.

As used herein, the term "RISC" refers to the RNA induced silencing complex.

As used herein, the term "RNAi agent" refers to any molecule that activates the RISC pathway.

RNAi agents include, but are not limited to siRNA and asRNA.

As used herein, the term "RNAi activity" refers to the ability of an RNAi agent to effect cleavage of a target nucleic acid.

As used herein, the term "Ago2 activity" refers to the ability of an RNAi agent to activate Ago2 to effect cleavage of a target nucleic acid. In certain embodiments, such Ago2 activity may be in a cell or may be in a cell free assay.

As used herein, the term "RNAi potency" refers to the ability of an RNAi agent to effect cleavage of a target nucleic acid or to otherwise modulate the amount of target protein in a cell or in an animal. Such cleavage or protein modulation may be measured directly or indirectly.

As used herein, the term "siRNA" refers to an RNAi agent that is a double stranded oligonucleotide.

As used herein, the term "asRNA" refers to an RNAi agent that is a single stranded oligonucleotide.

As used herein, the term "oligonucleotide" refers to a compound comprising a plurality of linked nucleotides or nucleosides. In certain embodiment, one or more nucleotides of an oligonucleotide is modified. In certain embodiments, an oligonucleotide comprises ribonucleic acid (RNA) or deoxyribonucleic acid (DNA). In certain embodiments, oligonucleotides are composed of natural and/or modified nucleobases, sugars and covalent internucleoside linkages, and may further include non-nucleic acid conjugates.

As used herein, the term "nucleoside" means a glycosylamine comprising a nucleobase and a sugar. Nucleosides includes, but are not limited to, natural nucleosides, abasic nucleosides, modified nucleosides, and nucleosides having mimetic bases and/or sugar groups.

As used herein, the term "natural nucleoside" or "unmodified nucleoside" means a nucleoside comprising a natural nucleobase and a natural sugar. Natural nucleosides include RNA and DNA nucleosides.

As used herein, the term "natural sugar" refers to a sugar of a nucleoside that is unmodified from its naturally occurring form in RNA (2'-OH) or DNA (2'-H).

As used herein, the term "nucleobase" refers to the base portion of a nucleoside or nucleotide. A nucleobase may comprise any atom or group of atoms capable of hydrogen bonding to a base of another nucleic acid.

As used herein, the term "natural nucleobase" refers to a nucleobase that is unmodified from its naturally occurring form in RNA or DNA.

As used herein, the term "heterocyclic base moiety" refers to a nucleobase comprising a heterocycle.

As used herein "oligonucleoside" refers to an oligonucleotide in which the internucleoside linkages do not contain a phosphorus atom.

As used herein "internucleoside linkage" refers to a covalent linkage between adjacent nucleosides.

As used herein "natural internucleotide linkage" refers to a 3' to 5' phosphodiester linkage.

As used herein, the term "modified internculeoside linkage" refers to any linkage between nucleosides or nucleotides other than a naturally occurring internucleoside linkage.

As used herein, the term "antisense compound" refers to an oligomeric compound that is at least partially complementary to a target nucleic acid molecule to which it hybridizes. In certain embodiments, an antisense compound modulates (increases or decreases) expression of a target nucleic acid.

As used herein, the term "antisense oligonucleotide" refers to an antisense compound that is an oligonucleotide.

As used herein, the term "antisense activity" refers to any detectable and/or measurable activity attributable to the hybridization of an antisense compound to its target nucleic acid. Such detection and or measuring may be direct or indirect. For example, in certain embodiments, antisense activity is assessed by detecting and or measuring the amount of target protein. In certain embodiments, antisense activity is assessed by detecting and/or measuring the amount of target nucleic acids and/or cleaved target nucleic acids and/or alternatively spliced target nucleic acids. In certain embodiments, antisense activity is mediated by RNase H, by RISC or by interfering with normal splicing of a pre-mRNA.

As used herein the term "detecting RNAi activity" or "measuring RNAi activity" means that a test for detecting or measuring RNAi activity is performed on a sample. Such detection and/or measuring may include values of zero. Thus, if a test for detection of RNAi activity results in a finding of no RNAi activity (RNAi activity of zero), the step of "detecting RNAi activity" has nevertheless been performed.

As used herein the term "control sample" refers to a sample that has not been contacted with a test compound. In certain embodiments, a control sample is obtained prior to administration of a compound to an animal. In certain embodiments, a control sample is obtained from an animal to which compound is not administered. In certain embodiments, a reference standard is used as a surrogate for a control sample.

As used herein the term "chimeric oligonucleotide" refers to an oligonucleotide, having at least one sugar, nucleobase and/or internucleoside linkage that is differentially modified as compared to the other sugars, nucleobases and internucleoside linkages within the same oligonucleotide. The remainder of the sugars, nucleobases and internucleoside linkages can be independently modified or unmodified. In general a chimeric oligonucleotide will have modified nucleosides that can be in isolated positions or grouped together in regions that will define a particular motif. Any combination of modifications and or mimetic groups can comprise a chimeric oligomeric compound as described herein.

As used herein, the term "motif" refers to a pattern of unmodified and modified nucleotides or linkages in an oligonucleotide.

As used herein, the term "mixed-backbone oligonucleotide" refers to an oligonucleotide wherein at least one internucleoside linkage of the oligonucleotide is different from at least one other internucleotide linkage of the oligonucleotide.

As used herein, the term "target protein" refers to a protein, the modulation of which is desired.

As used herein, the term "target gene" refers to a gene encoding a target.

As used herein, the term "target nucleic acid" refers to any nucleic acid molecule, the amount or function of which is capable of being modulated. Target nucleic acids include, but are not limited to, RNA (including, but not limited to pre-mRNA and mRNA or portions thereof), cDNA derived from such RNA, as well as non-translated RNA, such as miRNA. For example, in certain embodiments, a target nucleic acid can be a cellular gene (or mRNA transcribed from such gene) whose expression is associated with a particular disorder or disease state, or a nucleic acid molecule from an infectious agent.

As used herein, the term "targeting" or "targeted to" refers to the association of an antisense compound to a particular target nucleic acid molecule or a particular region of nucleotides within a target nucleic acid molecule.

As used herein, "designing" or "designed to" refer to the process of designing an oligomeric compound that specifically hybridizes with a selected target nucleic acid molecule.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% nucleobase complementary to a target nucleic acid.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site. In certain embodiments, an oligomeric compound specifically hybridizes with its target under stringent hybridization conditions.

As used herein, the term "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

As used herein, the term "modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

As used herein, the term "expression" refers to all the functions and steps by which a gene's coded information is converted into structures present and operating in a cell. Such structures include, but are not limited to the products of transcription and translation.

As used herein, "high-affinity modified monomer" refers to a monomer having at least one modified nucleobase, internucleoside linkage or sugar moiety, when compared to naturally occurring monomers, such that the modification increases the affinity of an antisense compound comprising the high-affinity modified monomer to its target nucleic acid. High-affinity modifications include, but are not limited to, monomers (e.g., nucleosides and nucleotides) comprising 2'-modified sugars.

As used herein, the term "2'-modified" or "2'-substituted" means a sugar of a nucleoside comprising a substituent at the 2' position other than H or OH.

As used herein, the term "MOE" refers to a 2'-O-methoxyethyl substituent.

As used herein, the term "high-affinity modified nucleotide" refers to a nucleotide having at least one modified nucleobase, internucleoside linkage or sugar moiety, such that the modification increases the affinity of an antisense compound comprising the modified nucleotide to a target nucleic acid. High-affinity modifications include, but are not limited to, BNAs, LNAs and 2'-MOE.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein, the term "bicyclic nucleic acid" or "BNA" refers to a nucleoside wherein the furanose portion of the nucleoside includes a bridge connecting two atoms on the furanose ring, thereby forming a bicyclic ring system. BNAs include, but are not limited to, α-L-LNA, β-D-LNA, ENA, Oxyamino BNA (2'-O—N(CH$_3$)—CH$_2$-4') and Aminooxy BNA (2'-N(CH$_3$)—O—CH$_2$-4').

As used herein, a "locked nucleic acid" or "LNA" refers to a nucleotide modified such that the 2'-hydroxyl group of the ribosyl sugar ring is linked to the 4' carbon atom of the sugar ring, thereby forming a 2'-C,4'-C-oxymethylene linkage. LNAs include, but are not limited to, α-L-LNA, and 13-D-LNA.

As used herein, the term "cap structure" or "terminal cap moiety" refers to chemical modifications, which have been incorporated at either terminus of an antisense compound.

As used herein, the term "animal" refers to a human or non-human animal, including, but not limited to, mice, rats, rabbits, dogs, cats, pigs, and non-human primates, including, but not limited to, monkeys and chimpanzees.

Overview

In certain embodiments, the present invention provides methods of predicting potency of an RNAi agent. In certain embodiments, such methods comprise determining the binding affinity of the RNAi agent with Ago2. In certain embodiments, such methods comprise determining the Ago2 activity of an RNAi agent. In certain embodiments, such determinations are made relative to a control and/or a reference standard. In certain embodiments, relative potency of two RNAi agents is predicted or assessed. In certain such embodiments, a competition assay is performed, wherein two RNAi agents are in competition with Ago2 and Ago2 binding and/or Ago2 activity is measured.

In certain embodiments the amount of Ago2 or the amount of Ago2 activity present in a cell is the rate limiting factor in RNAi activity. In certain cell types, Ago2 is the least abundant protein component of the RISC pathway. In certain embodiments, suppression of other members of the RISC pathway has little or no effect on RNAi activity. Accordingly, in certain such embodiments, RNAi activity correlates with Ago2 activity and/or with Ago2 binding. Thus, in certain embodiments, measuring Ago2 binding and/or Ago2 activity predicts RNAi activity and RNAi potency in a cell or tissue for a particular RNAi agent.

In certain embodiments, Ago2 binding of an RNAi agent is assessed. In certain such embodiments, Ago2 binding of an RNAi agent is assessed in a cell. In certain such embodiments, an RNAi agent is contacted with a cell to allow it to bind to Ago2 inside the cell; Ago2 is then precipitated from the cell and binding of the RNAi agent with the Ago2 is assessed. In certain embodiments, Ago2 binding of an RNAi agent is assessed in a cell-free assay. In certain such embodiments, Ago2 is contacted with an RNAi agent. In certain such embodiments, the Ago2 is obtained from immunoprecipitation from a cell. In certain such embodiments, Ago2 is overexpressed in the cell prior to immunoprecipitation. In certain embodiments the Ago2 is recombinant. In certain such embodiments, the recombinant Ago2 is isolated and purified. In certain embodiments, Ago2 binding of an RNAi agent correlates with Ago2 activity, with RNAi activity and/or RNAi potency. Accordingly, such Ago2 binding determination may be used to predict Ago2 activity, RNAi activity, and/or RNAi potency.

In certain embodiments, Ago2 activity of an RNAi agent is assessed. In certain such embodiments, Ago2 activity of an RNAi agent is assessed in a cell. In certain such embodiments, an RNAi agent is contacted with a cell to allow it to bind to Ago2 inside the cell; Ago2 is then precipitated from the cell and Ago2 activity is assessed. In certain such embodiments, Ago2 activity is assessed by contacting the precipitated Ago2/RNAi agent complex with a substrate RNA and detecting cleavage of the RNA substrate. In certain embodiments, Ago2 activity of an RNAi agent is assessed in a cell free assay. In certain such embodiments, Ago2 is contacted with an RNAi agent and with a substrate RNA and cleavage of the substrate RNA is detected. In certain such embodiments, the Ago2 is obtained from immunoprecipitation from a cell. In certain such embodiments, Ago2 is overexpressed in the cell prior to immunoprecipitation. In certain embodiments the Ago2 is recombinant. In certain such embodiments, the recombinant Ago2 is isolated and purified. In certain embodiments, Ago2 activity of an RNAi agent correlates with Ago2 binding, with RNAi activity and/or RNAi potency. Accordingly, such Ago2 activity determination may be used to predict Ago2 binding, RNAi activity, and/or RNAi potency.

In certain embodiments, the present invention provides competition assays. In certain such embodiments, assays to detect Ago2 binding or Ago2 activity described above are performed with two RNAi agents. In certain embodiments, such assays include test samples of varying concentrations of one or both of the RNAi agents. In certain embodiments, one of the RNAi agents in a competition assay is an RNAi agent of known Ago2 binding, Ago2 activity, and/or Ago2 potency (known competitor). In certain such embodiments, Ago2 binding or Ago2 activity of the known competitor is assessed. In certain embodiments, the ability of a test RNAi agent to inhibit Ago2 binding or Ago2 activity of the known competitor indicates that it has desirable binding, activity, and/or potency. In certain embodiments, the invention provides an assay system whereby two or more test RNAi agents are separately tested for their ability to compete against the same known competitor. In such embodiments, binding or activity of the two or more test RNAi agents may be compared by comparing their ability to inhibit binding or activity of the known competitor.

In certain such embodiments, (1) cells or Ago2 (from immunoprecipitation or recombinant) is placed in a multiwell plate; (2) a known competitor RNAi agent is added to each well at the same concentration per well; (3) a test RNAi agent is added to each of several wells, typically at several different concentrations; and (4) Ago2 activity or binding of either the known competitor RNAi agent or the test RNAi agent or both is detected and/or measured. In certain embodiments, such assays are useful for assessing the relative RNAi activity or potency of the test RNAi agent compared to the known competitor RNAi agent or compared to another test RNAi agent that is tested using the same known competitor RNAi agent. In certain embodiments, the concentration of the known competitor RNAi agent is varied and the concentration of the test RNAi agent is the same for each well. In certain embodiments, two or more competitor oligomeric compounds are separately tested against the same known competitor RNAi agent to assess the relative uptake of the two or more test RNAi agents. In certain embodiments, the known competitor RNAi agent is replaced with a second test RNAi agent. In such embodiments, one may measure or detect binding of one or both of the test RNAi agents. One of ordinary skill in the art will readily appreciate that these components can be manipulated in a variety of ways. Certain competition assays have been described previously. See e.g., Koller et al., Nucleic Acid Research, 34:16, 4467-4476 (2006), which is hereby incorporated by reference in its entirety.

Certain RNAi Agents

In certain embodiments, the present invention provides methods of predicting or assessing RNAi activity and/or RNAi potency of an RNAi agent. Such methods may be performed using any molecule suspected of having RNAi activity. In certain embodiments, an RNAi agent may be a synthetic small molecule or a peptide. In certain embodiments, RNAi agents are oligonucleotides. Such oligonucleotides may be single stranded or they may be double stranded. RNAi agents may comprise oligonucleotides that are modified. In the case of double-stranded oligonucleotide RNAi agents, one or both strands may be modified. If only one strand of a double stranded RNAi agent is modified, the modified strand may be a sense strand or it may be an antisense strand.

Certain RNAi agents have greater RNAi activity and RNAi potency than others. Certain siRNAs and asRNAs likewise have greater RNAi activity and RNAi potency than others. Such differences may be attributable to differences in length, chemical modification, sequence, target, or a combination of these and other factors.

In certain instances, it appears that the difference in potency is attributable to sequence. In certain competition assays, certain siRNAs demonstrate greater ability to compete. For example, when a PTEN siRNA is co-administered with an Eg5 siRNA, the PTEN siRNA consistently led to the degradation of PTEN mRNA and reduced the degradation of Eg5 RNA directed by the Eg5 siRNA. Both siRNAs were blunt-ended 19mer duplexes of unmodified RNA, transfected simultaneously into the same cells, so the competitive advantage enjoyed by the PTEN siRNA must be due to its sequence relative to the Eg5 sequence. Thus, in certain embodiments, the present invention provides a competition assay to identify and/or predict potent RNAi agents based on their ability to compete with another RNAi agent. In certain embodiments, the two RNAi agents tested in a competition assay have the same length and motif. In certain embodiments, RNAi agents tested in a competition assay have one or more differences in length and motif.

In certain embodiments, the present invention provides methods for predicting or assessing RNAi activity of single or double stranded oligonucleotides comprising different motifs. In certain embodiments, the present invention provides methods for predicting or assessing RNAi activity of single or double stranded oligonucleotides comprising different modifications. Such motifs and modifications include, but are not limited to, oligonucleotides comprising modified bases, modified internucleoside linkages and modified sugars.

In certain embodiments, an RNAi agent comprises a single or double stranded oligonucleotide comprising one or more modified nucleoside comprising a modified sugar. In such embodiments, the furanosyl sugar ring of the nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position.

BNA's have been prepared and disclosed in the patent literature as well as in scientific literature (Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; WO 94/14226; WO 2005/021570; Singh et al., J. Org. Chem., 1998, 63, 10035-10039; Examples of issued US patents and published applications that disclose BNAs include, for example, U.S. Pat. Nos. 7,053,207; 6,268,490; 6,770,748; 6,794,499; 7,034,133; and 6,525,191; and U.S. Pre-Grant Publication Nos. 2004-0171570; 2004-0219565; 2004-0014959; 2003-0207841; 2004-0143114; and 20030082807.

In certain embodiments, RNAi agents may comprise one or more "Locked Nucleic Acids" (LNAs) nucleosides, in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pats. Nos. 6,268,490 and 6,670,461). The linkage can be a methylene (—$CH_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

An isomer of LNA that may be used in certain embodiments, is alpha-L-LNA which has been shown to have superior stability against a 3'-exonuclease. The alpha-L-LNA's were incorporated into antisense gapmers and chimeras that showed potent antisense activity (Frieden et al., Nucleic Acids Research, 2003, 21, 6365-6372).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Certain modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-($CH_2$)$_2$—O-2' bridge); substituted sugars, especially 2'-substituted sugars having a 2'-F, 2'-$OCH_3$ or a 2'-O($CH_2$)$_2$—$OCH_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pats. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and 6,600,032; and WO 2005/121371. BNAs and 2' Modifications.

In certain embodiments, 2' modifications that may be assessed include, but are not limited to: halo, allyl, amino, azido, amino, SH, CN, OCN, $CF_3$, $OCF_3$, O—, S—, or N($R_m$)-alkyl; O—, S—, or N($R_m$)— alkenyl; O—, S— or N($R_m$)-alkynyl; O-alkylenyl-O-alkyl, alkynyl, alkaryl, aralkyl, O-alkaryl, O-aralkyl, O($CH_2$)$_2$$SCH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with substituent groups selected from hydroxyl, amino, alkoxy, carboxy, benzyl, phenyl, nitro ($NO_2$), thiol, thioalkoxy (S-alkyl), halogen, alkyl, aryl, alkenyl and alkynyl where each $R_m$ is, independently, H, an amino protecting group or substituted or unsubstituted $C_1$-$C_{10}$ alkyl.

In certain embodiments, 2' modifications that may be assessed include, but are not limited to F, —$NH_2$, $N_3$, O—$CH_3$, O($CH_2$)$_3$$NH_2$), $CH_2$—CH=$CH_2$, —O—$CH_2$—CH=$CH_2$, $OCH_2CH_2OCH_3$, 2'-O($CH_2$)$_2$$SCH_3$, O—($CH_2$)$_2$—O—N($R_m$)($R_n$), —O($CH_2$)$_2$—O—($CH_2$)$_2$N($CH_3$)$_2$, and N-substituted acetamide (O—$CH_2$—C(=O)—N($R_m$)($R_n$) where each $R_m$ and $R_n$ is, independently, H, an amino protecting group or substituted or unsubstituted $C_1$-$C_{10}$ alkyl. Another list of 2'-substituent groups includes F, $OCF_3$, O—$CH_3$, $OCH_2CH_2OCH_3$, 2'—O($CH_2$)$_2$$SCH_3$, O—($CH_2$)$_2$—O—N($R_m$)($R_n$), —O($CH_2$)$_2$—O—($CH_2$)$_2$N($CH_3$)$_2$, and N-substituted acetamides (O—$CH_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, assays of the present invention may be used to predict or assess RNAi activity or potency of a novel compound comprising novel modifications.

Certain RNAi Sequences

In certain embodiments, the present invention provides a method of identifying sequences with RNAi activity and/or potency. In certain such embodiments, the sequence comprises a plurality of pyrimidines in the seed region. The "seed region" is the second through the eighth nucleoside counting from the 5' end of a guide strand of an siRNA or of a single stranded oligonucleotide RNAi agent. In certain embodiments, a sequence having RNAi activity has at least 3, at least 4, at least 5, at least 6, or at least 7 pyrimidines in the seed region.

The sequence of the PTEN and Eg5 guide strands are 5'-UUGUCUCUGGUCCUUACUU-3' and 5'-AUAGACU-UCAUCCUUGUUG-3' respectively. The PTEN siRNA was a better competitor and had greater Ago2 binding, Ago2 activity, RNAi activity, and RNAi potency than the Eg5 siRNA, even though the two siRNAs had the same length and modification motif. The difference may be attributable to the greater pyrimidine content of the seed region of the PTEN sequence.

For all oligonucleotide compounds discussed herein, sequence, nucleoside, nucleoside modification, and internucleoside linkage may each be selected independently. In certain embodiments, RNAi agents are described by a motif. In such embodiments, any motif may be used with any sequence, whether or not the sequence and/or the motif is specifically disclosed herein. The sequence listing accompanying this filing provides certain nucleic acid sequences independent of chemical modification. Though that listing identifies each sequence as either "RNA" or "DNA" as required, in reality, those sequences may be modified with any combination of chemical modifications and/or motifs.

Certain Cells

In certain embodiments, the present invention provides cell based assays. In such embodiments, suitable cell include, but are not limited to HeLa, U87, and T47D cells. In certain embodiments, the present invention provides a method of selecting a target cell or tissue for RNAi, including, but not limited to RNAi based therapy, comprising selecting a cell or tissue type with a relatively high concentration of Ago2.

In certain embodiments, the invention provides cell based assays in which an RNAi agent is transfected into a cell, Ago2 binding and/or Ago2 activity occurs in the cell and is assessed. In certain embodiments, an RNAi agent is transfected into a cell and binding occurs in the cell and then cell is lysed allowing the Ago2 bound to the RNAi agent to be collected and assessed in a cell-free system. Thus, in certain embodiments, activity is assessed outside a cell after binding has occurred inside a cell. In certain of such embodiments, Ago2 is over-expressed in the cell prior to transfection of the RNAi agent.

In certain embodiments, the invention provides cell free assays. In certain such embodiments, Ago2 is contacted with an RNAi agent outside a cell. In certain such embodiments, the Ago2 is obtained by immunoprecipitating it from a cell. In certain such embodiments, the Ago2 is overexpressed in the cell prior to immunoprecipitation. In certain embodiments, the Ago2 is recombinant Ago2. Ago2 that is obtained by immunoprecipitation is expected to remain in association with certain other factors or proteins such as TRBP. The present inventors have shown that in certain instances recombinant Ago2 has comparable binding and activity.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

EXAMPLES

Example 1

Cells and Reagents

Tissue culture medium, trypsin and Lipofectamine-2000 were purchased from Invitrogen (Carlsbad, Calif.). HeLa, T47D and U87-MG cells were obtained from the American Type Tissue Collection (Manassas, Va.) and cultured in DMEM supplemented with 10% fetal calf serum, streptomycin (0.1 µg/ml), and penicillin (100 units/ml). Treatment of cells with siRNA and RNAseH ASOs was performed using Opti-MEM (Invitrogen) containing 2-5 µg/ml Lipofectamine 2000 and the indicated amount of siRNA/ASO for 3-5 h at 37° C., as described previously (Dean and Griffey, Antisense Nucleic Acid Drug Dev., 7, 229-233). For the generation of $IC_{50}$ curves cells were treated at doses ranging from 2 pM to 60 nM in half-log serial dilutions (N=4-8/dose). $IC_{50}$ curves and values were generated using Prism 4 software (Graph-Pad).

Example 2

Preparation of Antisense Oligonucleotides and siRNAs

Synthesis and purification of phosphorothioate/2'-MOE oligonucleotides was performed using an Applied Biosystems 380B automated DNA synthesizer. All ASOs were full phosphorothioate with 2'-O-methoxyethyl substitutions at positions 1-5 and 16-20 (boldface type). Residues 5-15 are unmodified 2'-oligodeoxynucleotides, so they can serve as substrates for RNase H. The sequences are as follows. Ago2 (ISIS136764), CTGCTGGAATGTTTCCACTT; Dicer (ISIS138648), GCTGACCTTTTTGCTTCTCA; TRBP (ISIS 237288), TGCGGTGGGCTGGCCCAGAC; Exportin5 (ISIS 350560), GTTACCATTCTGTACAGGTA. Silencer Pre-designed siRNAs for knockdown of RISC proteins were obtained from Ambion (Austin, Tex.). Ago2: siRNA ID#133832; Dicer: siRNA ID#137011; Exportin-5: siRNA ID#109277; TRBP: siRNA ID#139948. PTEN and Eg5 synthetic unmodified siRNAs were purchased from Dharmacon Research, Inc (Boulder, Colo.). siRNA duplexes were formed according to the manufacture's instructions. In brief, 1.6 µl of a 250 µM antisense stock was combined with 1.6 µl of a 250 µM sense stock, 4 µl of 5× universal buffer (500 mM potassium acetate, 150 mM HEPES-KOH, pH 7.4, 10 mM magnesium acetate) and 12.8 µl of ultrapure water followed by heating at 90 C for one minute. The reaction was then allowed to cool to ambient temperature. The final concentration of the duplex was 20 µM in 1× universal buffer (100 mM potassium acetate, 30 mM HEPES-KOH, pH 7.4, 2 mM magnesium acetate). The sequence of the PTEN siRNA is AAGTAAGGACCAGAGACAA (sense) and TTGTCTCTGGTCCTTACTT (antisense). The sequence of the Eg5 siRNA is CAACAAGGATGAAGTCTAT(sense) and ATAGACTTCATCCTTGTTG (antisense).

Example 3

Taqman RT-PCR

Quantitative RT-PCR was performed essentially as described elsewhere. See Winer, et al., Anal. Biochem., 270, 41-19 (1999). Briefly, 200 ng of total RNA was analyzed in a final volume of 50 µl containing 200 nM gene-specific PCR primers, 0.2 mM of each dNTP, 75 nM fluorescently labeled oligonucleotide probe, 5 µl RT-PCR buffer, 5 mM MgCl2, 2 U of Platinum TaqDNA Polymerase (Invitrogen Life Technologies), and 8 U of RNase inhibitor. Reverse transcription was performed for 30 min at 48° C. followed by PCR: 40 thermal cycles of 30 s at 94° C. and 1 minute at 60° C. using an ABI Prism 7700 Sequence Detector (Applied Biosystems). The sequence for the human Ago2 primer/probe set used in the RT-PCR reaction was CCAGCTACACTCAGACCAA-CAGA for the forward primer, GAAAACG-GAGAATCTAATAAAATCAATGAC for the reverse primer and CGTGACAGCCAGCATCGAACATGAGA for the probe. The sequence for the human Dicer primer/probe set used in the RT-PCR reaction was ATTAACCTTTTGGT-GTTTGATGAGTGT for the forward primer, GCGAGGA-CATGATGGACAAATT for the reverse primer and ATCT-TGCAATCCTAGACCACCCCTATCGAGAA for the probe. The sequence for the human TRBP primer/probe set used in the RT-PCR reaction was CAGCCCACCGCAAAGAAT for the forward primer, TGCCACTCCCAATCTCAATG for the reverse primer and CACCATGACCTGTCGAGTG-GAGCGT for the probe. The sequence for the human Exportin 5 primer/probe set used in the RT-PCR reaction was GCT-GTGAATATTCTCGGTTTGATTT for the forward primer, GGAAGCTAGTTTTGGGATCCAA for the reverse primer and TCCTCCCGAGCACAACAAGGAGAGG for the probe.

Example 4

Western Blotting

Whole cell extracts were prepared by lysing cells in radioimmunoprecipitation assay (RIPA) buffer (1×PBS, 1% Nonidet P-40, 0.1% deoxycholate, and 0.1% SDS containing complete protease inhibitor mix (Boehringer Mannheim). Protein concentration of the cell extracts was measured by Bradford assay (no. 500-0201; Bio-Rad). Equal amounts of protein (10-20 µg) were resolved on a NuPAGE Novex 8-16% Trisglycine gel in Tris-Gly SDS running buffer (Invitrogen Life Technologies) and transferred to polyvinylidene difluoride membranes (Invitrogen Life Technologies). The membranes were blocked for 1 hour in TBS containing 0.05% Tween 20 (TBST) and 5% milk powder. After overnight incubation at 4° C. with a 1/1000 dilution of a mouse monoclonal antibody to Ago2, Exportin 5 (Abnova), Dicer [13D6] (Abeam), or a 1/3000 dilution of a rabbit polyclonal antibody to TRBP, the membranes were washed in PBS containing 0.05% Tween 20 and incubated with a 1/5000 dilution of goat anti-rabbit or goat anti-mouse HRP-conjugated Ab in blocking buffer. Membranes were washed and developed using ECL detection system (Amersham Biosciences). Subsequently, membranes were blocked for 2 h at room temperature in TBST plus 5% milk powder. After incubation at room temperature with a 1/5000 dilution of a mouse monoclonal tubulin Ab (no. T-5168; Sigma-Aldrich), the membranes were washed in PBS containing 0.1% Tween 20 and incubated with a 1/5000 dilution of goat anti-mouse HRP-conjugated Ab in blocking buffer and developed as detailed above and exposed to film (Kodak).

Example 5

RISC Protein Overexpression and Reduction

Plasmids expressing Dicer and Exportin 5 under the control of the CMV promoter were obtained from OriGene Technologies, Inc. (Rockville, Md.). cDNAs for Ago2 and TRBP were isolated from HeLa cell cDNA by PCR and cloned into pcDNA3.1 (Invitrogen). For RISC gene overexpression assays, 10 ug of plasmid was introduced into cells at 50% confluence in 10-cm dishes using SuperFect Reagent (Qiagen). Following a 3 hour treatment, plasmid was removed and fresh DMEM added to the cells. Following an overnight incubation cells were trypsinized then seeded in 96 well plates at 4000-6000 cells per well. Cells were allowed to adhere for 4 hours, then siRNAs were added in the presence of Lipofectamine 2000 reagent as detailed above. For siRNA competition experiments both siRNAs were premixed then added simultaneously to the cells. All siRNA/ASO treatments were performed in triplicate or quadruplicate. Following the 5 hour transfection, siRNAs were aspirated and fresh DMEM added to the cells. Treated cells were incubated overnight. The next day total RNA was purified from 96-well plates using an RNeasy 3000 BioRobot (Qiagen, Valencia, Calif.). Reduction of target mRNA expression was determined by real time RT-PCR using an ABI Prism 7700 Sequence Detector (Applied Biosystems, Foster City, Calif.). The sequence for the human Eg5 primer/probe set used in the RT-PCR reaction is GCCCCAAATGTGAAAGCATT for the forward primer, CTAAAGTGGGCTTTTTGTGAACTCT for the reverse primer and CCTTTAAGAGGCCTAACTC for the probe. The sequence for the human PTEN primer/probe set is AATGGCTAAGTGAAGATGACAAT for the forward primer, TGCACATATCATTACACCAG-TTCGT for the reverse primer and AGATGCCGTGTTTGATGGCTCCAGC for the probe. mRNA levels were normalized to total RNA for each sample as measured by Ribogreen (Invitrogen).

For RISC reduction, HeLa cells were seeded in 10 cm dishes at 650,000 cells per plate. The following day RISC specific siRNA/ASO (above) was added at 50 nM in Opti-MEM media in the presence of 5 ug/ml Lipofectamine 2000. Following a 5 hour incubation the transfection mixture was aspirated and DMEM added to the cells. The remainder of the experiment was carried out as described for the RISC overexpression studies above.

Example 6

Kinetic analysis of siRNA Competition

To analyze kinetics of RISC loading HeLa cells were seeded in 96 well plates at 4500/well. The following day cells were transfected with 300 pM Eg5 siRNA using Opti-MEM media containing 5 µg/ml Lipofectamine 2000. The Eg5/Lipofectamine 2000 complex was removed at timepoints between 0 and 240 minutes from the initiation of the transfection and replaced with a mixture of 300 pM Eg5 siRNA and 10 nM PTEN siRNA (N=4/timepoint). Cells were incubated 4 hours, then siRNA removed and fresh DMEM added. Cells were incubated overnight then total RNA was purified and Eg5 mRNA expression evaluated by qRT/PCR.

For RISC unloading kinetics HeLa cells were seeded in 96 well plates at a density of 4000 cells/well. The following day cells were transfected with 10 nM PTEN competitor siRNA in Opti-MEM media containing 3 µg/ml Lipofectamine 2000. After 3 hours the PTEN/Lipofectamine 2000 complex was removed, the cells washed with PBS, and fresh DMEM+5% FCS added. 20 nM complexed with 5 µg/ml Lipofectamine 2000, then 1/20 volume added directly to the pretreated cells (final concentration=1 nM) Immediately following the PTEN siRNA pretreatment and at intervals from 2-18 hours Eg5 siRNA was transfected at 300 pM as detailed above (N=8/timepoint). For each timepoint the siRNA/lipid complex was removed after 3 hours, cells washed with PBS, and fed with DMEM+10% FCS. Cells were incubated overnight then total RNA was purified and Eg5 mRNA expression evaluated by qRT/PCR. Where indicated the experiment was performed in the presence of 25 μg/ml cycloheximide (Sigma). Inhibition of protein synthesis was confirmed by measurement of cellular incorporation $^{35}$S-Translabel (MP Biomedicals).

For kinetic analysis of siRNA activity HeLa cells were seeded in 96 well plates then treated with 10 nM Eg5 siRNA as detailed above. Cells were harvested and total RNA isolated beginning at 15 minutes from the initiation of transfection. The transfection mixture was removed from cells at 4 hours for the 7 and 18 hour timepoints and complete media added. Eg5 and PTEN mRNA expression was assessed by qRT/PCR and normalized to total RNA as measured by ribogreen assay.

Example 7

Levels of siRNA Components in Various Cell Lines

Previous work has suggested that RISC components may be rate limiting as co-transfection of two siRNAs resulted in loss of activity (Koller et al., Nucleic Acid Research, 34:16, 4467-4476 (2006)). Ago2 has been shown to be required for siRNA activity in mammalian cells. Sontheimer, Nat Rev Mol Cell Biol., 6(2):127-38 (2005). Liu, et al., Science, 305, 1437-1441 (2004). Although Dicer and TRBP are clearly important and involved in the siRNA pathway, whether they are required for the activities of siRNAs is somewhat controversial. Two reports in which siRNAs were used to reduce Dicer and/or TRBP suggested that Dicer and TRBP were required for siRNA activity (Doi, et al., Curr. Biol., 13, 41-46 (2003) and Chendrimada, Nature 436, 740-44 (2005)), but studies in which the Dicer gene was knocked out suggested that Dicer was required for miRNA processing and activity, but not required for siRNA activity. See Kanellopoulou, et al., Genes Dev., 19 489-501 (2005); Murchison, et al., Proc. Natl. Acad. Sci. USA, 102, 12135-12140 (2005). It has been demonstrated that TRBP is required for the recruitment of Ago2 to the siRNA bound by Dicer (Chendrimada, Nature 436, 740-44 (2005)). In addition, it has recently been shown that the Exportin-5-based exclusion of siRNAs from the nucleus can, when Exportin-5 itself is inhibited, become a rate-limiting step for siRNA induced silencing activity. See Ohrt, et al., Nucleic Acids Res., 34, 1369-1380 (2006). In an attempt to correlate RISC levels with observed differences in siRNA competition and activity the expression levels of these genes were characterized in HeLa cells, an epithelial carcinoma cell line, T47D, a ductal carcinoma cell line, and U87-MG, and a glioblastoma cell line.

The relative expression levels of the messenger RNAs for the RISC related genes were measured by quantitative RT/PCR. The data was analyzed by comparing the levels of each mRNA to the levels in HeLa cells in order to estimate differences in relative levels of each mRNA between cell lines. While HeLa and U87-MG cells were found to have similar levels of Dicer and TRBP mRNA, levels of the same messages were 5-7 fold higher in T47Ds. Ago2 and Exportin-5 mRNAs were found to be reduced in U87-MG cells relative to HeLa and T47D cells which had roughly equivalent amounts of the same mRNAs.

The levels of Ago2, Dicer, TRBP and exportin-5 proteins were assessed by Western blot. Dicer and TRBP levels were comparable in U87-MG and HeLa cells, and Ago2 and Exportin-5 were lower in U87-MG cells, in agreement with the messenger RNA data. RISC expression was also evaluated in other cells lines and found to vary considerably. Of the cell lines tested, the highest levels of Ago2 were found in HeLa cells. T47D cells expressed Dicer and TRBP at the highest levels, while the lowest levels of Ago2 and Exportin-5 were found in U87-MGs.

Example 8

The Magnitude of PTEN and Eg5 siRNA competition In Various Cell Lines

It has previously been shown that an siRNA targeted to PTEN is an effective competitor of an siRNA targeted to Eg5 (Koller et al., Nucleic Acid Research, 34:16, 4467-4476 (2006)). To determine if siRNA competition could be correlated with differences in expression of the various RISC proteins, the activity of Eg5 siRNA was evaluated in the absence or presence of increasing amounts of PTEN siRNA in HeLa, T47D, and U87-MG cells. Cells were transfected with Eg5 siRNA at doses ranging between 20 pM and 20 nM alone or co-transfected with the PTEN competitor siRNA at doses of 2, 6, or 20 nM for 4 hours as detailed herein. Following transfection, cells were incubated overnight then harvested and total RNA isolated. Quantitative RT/PCR was performed to assess the reduction of Eg5 mRNA. In the absence of competitor siRNA (■), the $IC_{50}$ for siRNA mediated reduction of Eg5 was similar in HeLa and T47D cells (92±18 and 76±15 pM respectively) and approximately 2 fold higher in U87-MGs (198±45 pM). In all cell lines the $IC_{50}$'s for Eg5 inhibition increased when co-transfected with increasing amounts of PTEN competitor siRNA. In HeLa cells, competition with PTEN siRNA at the highest concentration of 20 nM (▲) resulted in an increase in the $IC_{50}$ for Eg5 siRNA to 772±227 pM, approximately 8 fold higher than observed in the absence of competitor (FIG. 1A). Similarly, in T47Ds, competition with 20 nM PTEN siRNA increased the $IC_{50}$ nearly 7 fold (FIG. 1B). In contrast, a similar magnitude of competition was achieved in U87 cells using only 6 nM PTEN siRNA competitor (●; $IC_{50}$=1.2±0.3 nM) and an over 20 fold increase in $IC_{50}$ was observed in the presence of 20 nM competitor ($IC_{50}$=4.4±2.1 nM, FIG. 1C). These data illustrate that the magnitude of PTEN and Eg5 competition varies between cell lines.

Example 9

Figure 2:
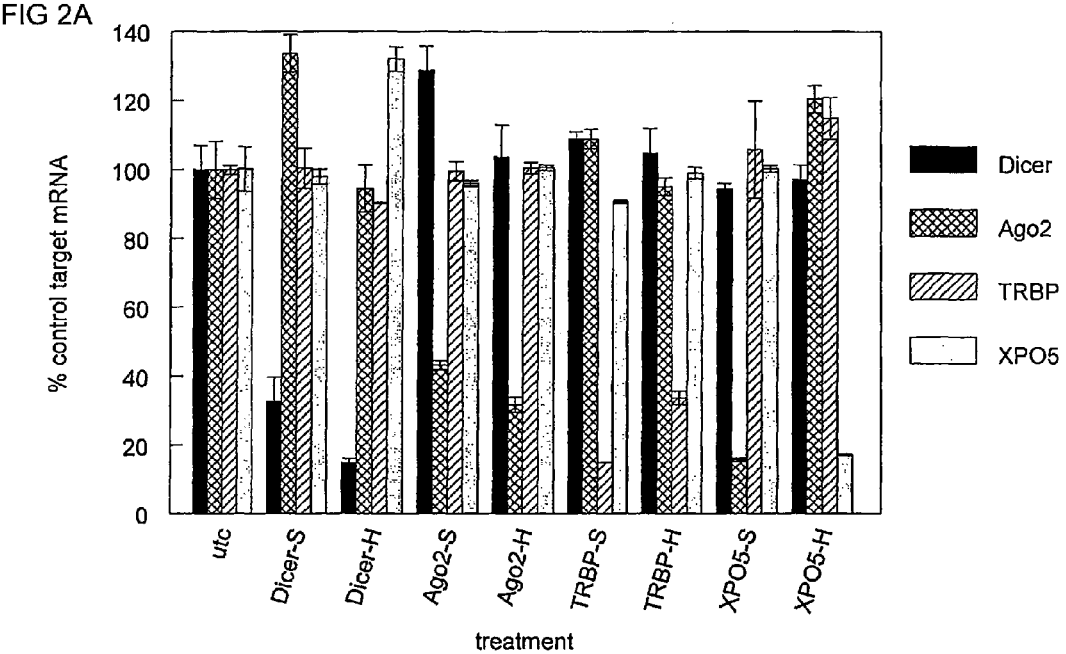
FIG. 2. RISC reduction and overexpression A) RISC mRNA reduction by RNAseH dependent antisense oligonucleotides and siRNAs. HeLa cells were treated with siRNAs or ASOs targeted to Dicer, Ago2, TRBP or exportin-5 at 50 nM. After 24 hours, cells were harvested and expression of the targeted mRNA determined by qRT/PCR. The results shown are the percent control relative to untreated cells. B) RISC overexpression. HeLa cells were transfected with mammalian expression plasmids for human Dicer, Ago2, TRBP, or exportin-5. After 24 hours cells were harvested and lysates prepared for analysis of protein expression by Western blot. Duplicate lanes were loaded with 15 ug each of total protein. Tubulin mAb was used as a loading control.
Figure 2:
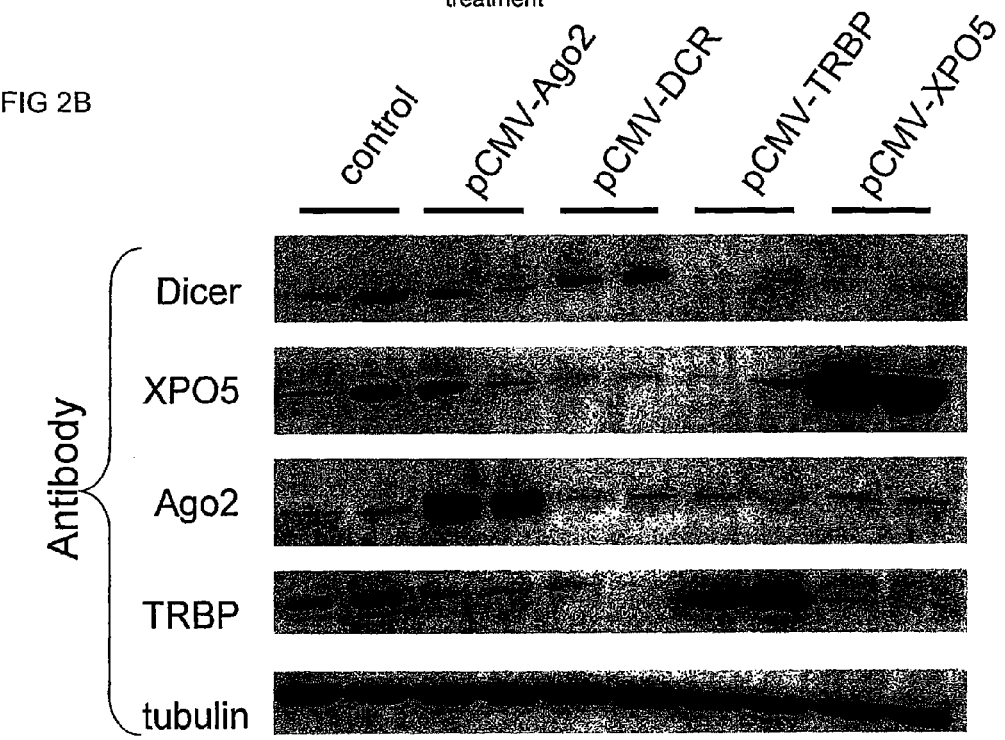

Comparison Ago2, Dicer, TRBP, and Exportin-5 Levels and siRNA Activity and Magnitude of Competition To determine if reduction in native levels of RISC components might result in changes in siRNA potency and competition, reduction of RISC components was effected using siRNA or RNaseH-dependent antisense oligonucleotide (ASO) inhibitors in HeLa cells. The reduction of each component and the evaluation of the activities of siRNAs in a single cell line eliminates any contribution of cell line to cell line variation in transfection efficiency which might result in apparent differences in RNA potency and competition. As shown in FIG. 2A, HeLa cells treated with either siRNA (S) or antisense (H) inhibitors showed a marked decrease in the targeted RISC mRNAs 24 hours after the initiation of transfection.

Figure 3:
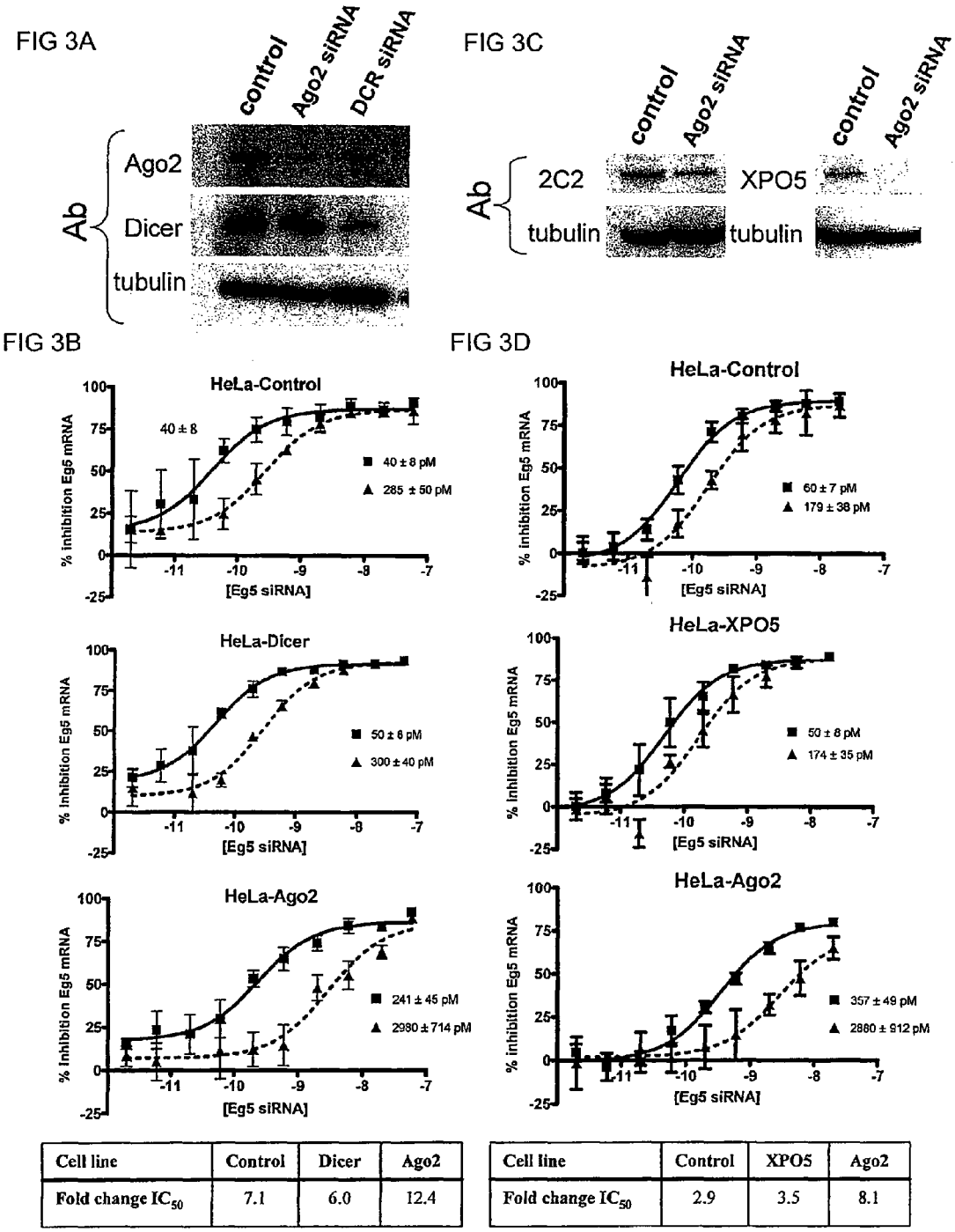
FIG. 3: Ago2 reduction effects both potency and magnitude of siRNA competition. HeLa cells were treated with siRNAs targeting Ago2, Dicer or XPO5. After 24 hours cells were seed in 96 well plates then treated 4 hours later cells at Eg5 siRNA doses from 2 pM to 60 nM in the presence or absence of 10 nM PTEN competitor siRNA for 4 hours. The following day $IC_{50}$s for Eg5 mRNA reduction were generated by qRT/PCR. A) Levels of Ago2 and Dicer reduction in siRNA treated cells were assessed by Western blot 24 hours after initiation of treatment. B) Eg5 $IC_{50}$ curves for HeLa cells in the presence (solid line) or absence (dotted line) of PTEN competitor siRNA. C) Levels of Ago2 and XPO5 reduction in siRNA treated cells were assessed by Western blot 24 hours after initiation of treatment. D) Eg5 $C_{50}$ curves for HeLas in the presence (solid line) or absence (dotted line) of PTEN competitor siRNA. Eg5 $C_{50}$s with standard error are shown in the absence (■) or presence (▲) of PTEN siRNA competitor. The fold change in $IC_{50}$ for each cell line is shown at the bottom of the figure.

The effects of Ago2 or Dicer protein reduction on siRNA competition and potency were initially evaluated in HeLa cells. Cells were treated with target specific siRNAs as detailed herein. 24 hours later cells were seeded in 96-well plates and $IC_{50}$s for Eg5 siRNA were assessed in the presence or absence of 15 nM PTEN siRNA competitor. Reductions in Ago2 and Dicer protein levels were confirmed at the time of Eg5 siRNA transfection by Western blot analysis (FIG. 3A). In cells without reduction of RISC components (FIG. 3B, top panel) the $IC_{50}$ for Eg5 siRNA in the absence of PTEN competitor was 40±8 pM (solid line), while in the presence of competitor the $IC_{50}$ was determined to be 285±50 pM (dotted line). Reduction of Dicer (middle panel) had little effect on the siRNA activity or competition in HeLa cells with $IC_{50}$s in the absence and presence of PTEN competitor of 50 f 8 pM and 300±40 pM respectively. In contrast, in cells in which Ago2 was reduced (lower panel), there was a significant change in both siRNA potency and competition. The $IC_{50}$ in the absence of PTEN competitor was determined to be 241±45 pM, while competition with PTEN siRNA in the same cells resulted in an $IC_{50}$ of 2.98±0.7 nM. Comparing the Eg5 $C_{50}$s in the absence of PTEN competition, there was a decrease in potency of approximately 6 fold in the cells treated with Ago2 ASO. In addition, the magnitude of PTEN competition was increased in these cells as the $IC_{50}$ in the presence of competitor was approximately 12 fold greater than in the absence of competitor, compared to approximately 7 fold in HeLa cells with normal Ago2 levels. Therefore, the magnitude of competition was almost 2 fold greater in HeLa cells in which Ago2 levels are reduced. It is also interesting to note that Ago2 reduction resulted in a change in siRNA potency and competition comparable to that observed in U87 cells and after reduction of Ago2 with siRNAs or ASOs the level of Ago2 in HeLa cells appears to be roughly comparable to the level in untreated U87 cells (compare with (FIG. 3C Table I).

In another experiment; HeLa cells were treated with siRNAs targeted to exportin-5 or Ago2. Reduction of targeted protein was confirmed after 24 hours by Western blot analysis (FIG. 3C). Reduction of exportin-5 had no effect on siRNA potency as the $IC_{50}$s for Eg5 reduction were nearly the same in both untreated (FIG. 3D, top panel) and exportin-5 reduced (middle panel) HeLas. The increases in $IC_{50}$'s in the presence of PTEN siRNA competitor were also nearly the same for untreated and exportin-5 reduced HeLa cells (compare dotted lines). Once again, in cells in which Ago2 was reduced (lower panel) there was a significant decrease in potency of Eg5 siRNA alone as the $IC_{50}$ increased from 61±7 pM in untreated HeLa cells to 357±49 pM in Ago2-reduced HeLa cells (compare solid curves). The magnitude of competition by the PTEN siRNA competitor was also increased in Ago2 reduced cells. In untreated HeLa cells, an approximately 3 fold increase in Eg5 siRNA $IC_{50}$ was observed in the presence of PTEN siRNA competitor. In contrast, the Eg5 siRNA $IC_{50}$ in the presence of PTEN siRNA was determined to be 2.9±0.9 nM, an approximate 8 fold increase in $IC_{50}$. In other experiments TRBP was targeted, and reduction of this protein had no effect on siRNA competition or potency while Ago2 reduction repeatedly and consistently resulted in decreases in siRNA potency and competition using either ASOs or siRNAs to effect protein reduction.

The effect of RISC protein overexpression on siRNA competition was also evaluated. As shown FIG. 2B, cells transfected with expression plasmids showed significant increases in Dicer, TRBP, Ago2, or exportin-5 protein 24 hours after the initiation of transfection. U87-MG control and Ago2 overexpressing cells were transfected with Eg5 siRNA at doses from 2 pM to 60 nM in the presence or absence of 5 nM PTEN siRNA competitor. The following day total RNA was isolated and $IC_{50}$s determined by qRT/PCR. Ago2 mRNA levels as determined by qRT/PCR also confirmed overexpression of the message in cells harboring the plasmid. Increased Ago2 expression in U87-MG cells resulted in an increase in siRNA potency with the $IC_{50}$ for Eg5 mRNA reduction decreasing from 291±79 pM in untreated U87-MG cells to 65±18 pM in cells overexpressing Ago2 (Table I). The $IC_{50}$ in the presence of PTEN siRNA increased in the untreated cells by approximately 5.6 fold to 1.6±0.5 nM. In the Ago2 transfected U87-MG cells the $IC_{50}$ was 138±40 pM, a 2.1 fold increase over the $IC_{50}$ obtained in cells with normal protein levels. Overexpression of the other proteins (FIG. 2B) had no effect on the potency of Eg5 siRNA or competition due to PTEN siRNA.

These data illustrated that Ago2 levels, but not Dicer, TRBP, or Exportin-5 levels, limit siRNA activity and the magnitude of siRNA competition.

Example 10

PTEN siRNA is a more Effective Competitor than Eg5 siRNA

It has previously been observed that there is, in general, a correlation between siRNA potency and competition, with more potent siRNAs being more effective competitors. (Koller et al., Nucleic Acid Research, 34:16, 4467-4476 (2006)). Having demonstrated that siRNA competition is dependant upon the availability of Ago2 within the cell, it was hypothesized that when Ago2 is limiting the siRNA with the greater affinity for Ago2 would be the more effective competitor. To test this hypothesis, competitive inhibition of Ago2 binding was employed to measure the relative binding affinities of the Eg5 and PTEN siRNAs as detailed herein. The $K_D$ for the PTEN sense strand was determined to be 92±17 nM (FIG. 4A, squares) while the $K_D$ for Eg5 was determined to be 671±138 nM. This approximately seven-fold difference in binding affinity was observed in separate experiments.

Figure 4:
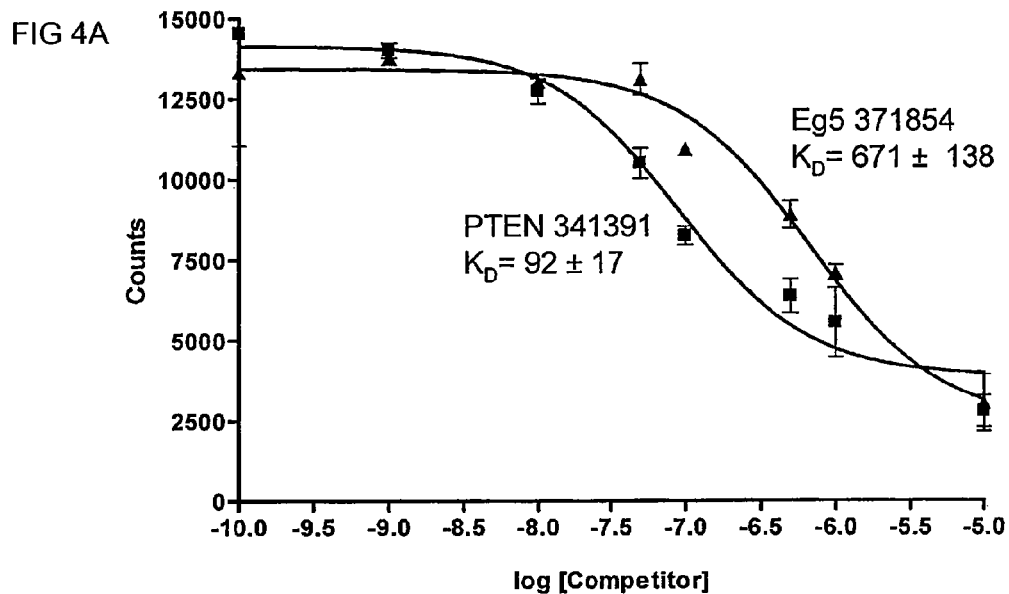
FIG. 4. siRNA potency and competition are related to relative affinities for Ago2. A) Competitive binding of Eg5 and PTEN siRNA guide strands to purified Ago2. B) $IC_{50}$'s in U87-Mg cells for PTEN siRNA competed with Eg5 siRNA at 0, 2, 6 and 20 nM as in FIG. 2.
Figure 4:
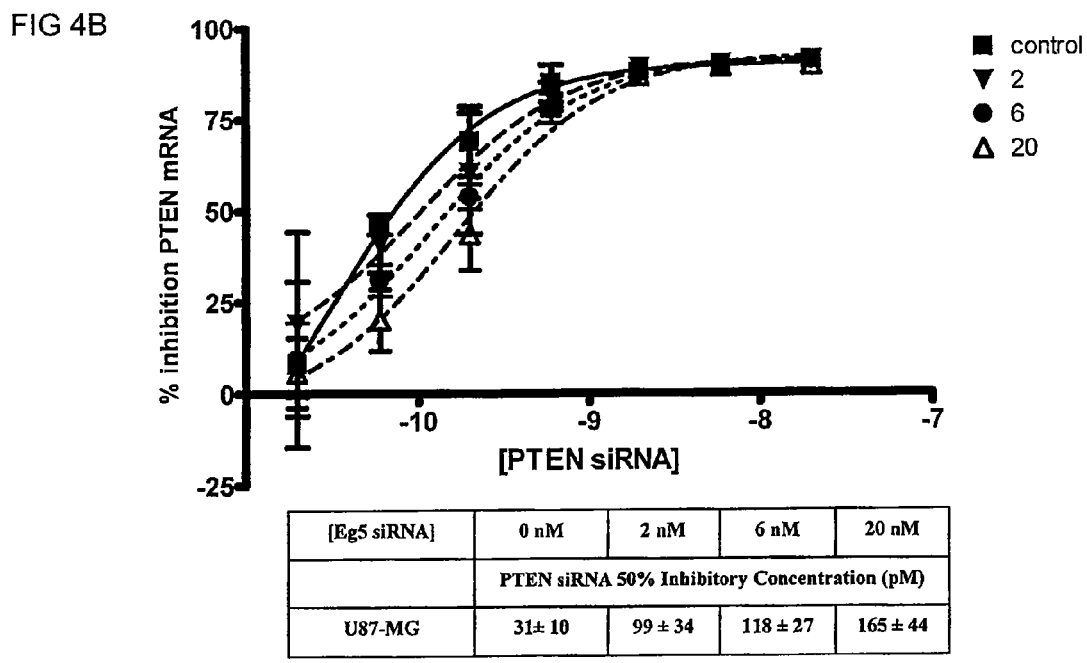

Competition between the same siRNAs was compared in U87 cells since they have the lowest Ago2 levels of the cell lines characterized. Cells were transfected PTEN siRNA ranging between 20 pM and 20 nM alone or in the presence of Eg5 competitor siRNA at doses of 0, 2, 6, or 20 nM as detailed above. $IC_{50}$ curves for PTEN siRNA alone and in the presence of Eg5 competitor are shown in FIG. 4B. The $IC_{50}$ for PTEN siRNA in the absence of competition was determined to be significantly lower (31±10 pM) than that of Eg5 siRNA alone (198±45 pM). In contrast to the strong competition observed when PTEN siRNA was used as a competitor of Eg5 siRNA with the $IC_{50}$ for Eg5 increasing by over 20 fold in cells treated with 20 nM PTEN siRNA (FIG. 1C, open triangles), when Eg5 siRNA was used as a competitor of PTEN siRNA only 5 fold change in $IC_{50}$ at the 20 nM dose of competitor (FIG. 4B). Eg5 siRNA was also a less effective competitor than PTEN at the 2 and 6 nM doses (inverted triangle and circles respectively).

These data illustrate that PTEN siRNA is a more effective competitor than Eg5 siRNA.

Example 11

Kinetics of RISC Loading and Unloading siRNA competition was used to evaluate the kinetics of RISC loading and unloading. To evaluate RISC loading, Eg5 siRNA activity was measured in the presence of the PTEN competitor siRNA added simultaneously or at various times after the initiation of transfection of the Eg5 siRNA. In the absence of PTEN siRNA competition, a 78.3±11.2% reduction of Eg5 message was observed in cells treated with 300 pM Eg5 siRNA, while in the presence of 10 nM PTEN siRNA competitor added simultaneously only 40.6±11.5% reduction was observed. When the addition of PTEN competitor siRNA was delayed from 5 to 30 minutes no effect on competition was observed. When addition of PTEN siRNA was delayed by 60 minutes the percent reduction of Eg5 siRNA increased to 65.8±12.5% and by 120 minutes no competition was observed with the percent reduction returning to levels comparable to those observed with Eg5 siRNA treatment alone. These results indicate that the Eg5 siRNA loaded and saturated the free RISC available in the cells in 1-2 hours. Once RISC was loaded the siRNA/RISC, the more potent PTEN siRNA, the guide strand of which displays higher affinity for purified Ago2, was unable to compete.

To evaluate unloading of RISC, HeLa cells were pre-treated for 3 hours with 15 nM PTEN siRNA. Cells were washed, then 300 pM Eg5 siRNA added at times following PTEN siRNA treatment. Eg5 siRNA transfections were carried out for 3 hours, then the cells incubated overnight. The following day RNA was purified and the percent reduction of Eg5 mRNA determined by qRT/PCR. Cells that were not pre-treated with PTEN siRNA (E) showed greater than 65% reduction of Eg5 mRNA (FIG. 5B). In contrast, cells pre-treated with PTEN siRNA displayed approximately 28% reduction of Eg5 mRNA at the same dose when the Eg5 siRNA was transfected immediately after PTEN siRNA treatment (T=0). After 2 hours the percent reduction was increased from 28% approximately 46% and increased to 55% by 9 hours. After 12 hours, no PTEN siRNA competition was observed with levels of Eg5 reduction returning to over 65%. To determine if the loss of competition resulted from unloading of RISC or because of new synthesis of Ago2, the effects of inhibiting protein synthesis in HeLa cells were determined in similar experiments. Cycloheximide (25 gg/mL) was added to cells following the PTEN siRNA pre-treatment. When cells were treated with cycloheximide, Eg5 mRNA reduction followed the same pattern as in the absence of cycloheximide (FIG. 5B, crosshatched bars). In the absence of competition almost 70% reduction of Eg5 mRNA was observed. At T=0 15 nM PTEN siRNA resulted in 42% reduction of Eg5 and by T=12 hours had returned to Eg5 siRNA-only levels. In these experiments, $S^{35}$ methionine incorporation was determined to be inhibited by greater than 95%. The similarity of recovery of Eg5 inhibition in the presence or absence of cycloheximide suggests that new protein synthesis is not required. Instead, RISC must in some manner be unloaded and recycled.

Figure 6:
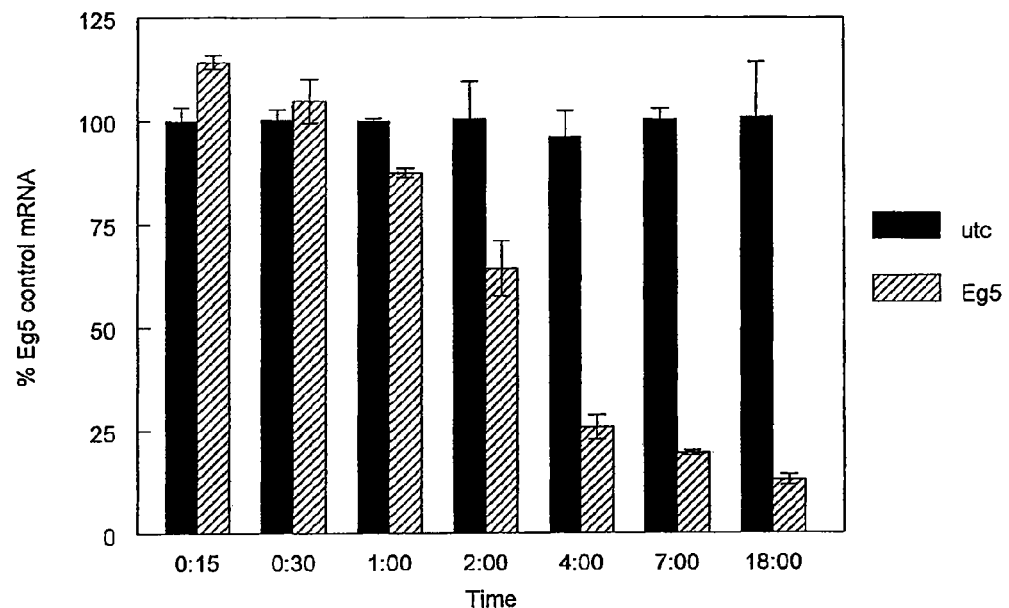
FIG. 6. Kinetics of mRNA reduction by Eg5 siRNA. HeLa cells were transfected with 10 nM Eg5 siRNA as detailed in Materials and Methods. siRNA treated and control cells were harvested and Eg5 mRNA reduction determined at the indicated times by qRT/PCR.

Together, these kinetic data indicate that RISC is loaded fairly rapidly within 2 hours of the initiation of transfection. Target cleavage, product release and RISC recycling is a slower process taking as long as 12 hours to complete. The kinetics of mRNA reduction by Eg5 siRNA were explored to determine if mRNA reduction followed a similar time course as RISC loading and recycling. HeLa cells were transfected with 10 nM Eg5 siRNA as detailed herein. Cells were harvested and Eg5 mRNA reduction determined beginning 15 minutes after the initiation of transfection. A slight reduction in Eg5 mRNA levels (FIG. 6, striped bars) was observed after 1 hour. By 2 hours Eg5 levels had been reduced by 35% and by 4 hours 76%. Maximal messenger RNA reduction was not observed until between 7 and 18 hours after the initiation of siRNA treatment. No Eg5 mRNA reduction was observed in untreated cells (FIG. 6, solid bars).

Example 12

Ago2 Activity Assay in Cells

Synthetic oligonucleotides were manufactured by Dharmacon Research, Inc. siRNA duplexes were formed according to the manufacturer's instructions. The final concentration of the duplex was 20 mM in 100 mM potassium acetate, 30 mM HEPES-KOH at pH 7.4, 2 mM magnesium acetate. The RNA substrates were 5'-end-labeled with $^{32}P$ using 10 U of T4 polynucleotide kinase. The labeled oligoribonucleotide was purified on a 12% denaturing polyacrylamide gel. The specific activity of the labeled oligonucleotide was approximately 3000 to 8000 cpm/fmol.

The cDNA of human Ago2 with an N-terminal HA epitope was subcloned into the mammalian expression vector phCMV-2. HeLa cells (CCL-2) were treated with the Ago2 expression plasmid using Effectene transfection reagent. The cells were then treated with 75 nM synthetic oligoribonucleotides or siRNAs using Lipofectamine 2000 reagent 24 h after the treatment with Ago2 expression plasmid and incubated for 18 h. Cells were harvested with Trypsin, then washed twice with 1 mL of cold PBS. The cell pellet was re-suspended in 500 mL of lysis buffer (150 mM NaCl, 0.5% NP-40, 2 mM MgCl2, 2 mM CaCl2, 20 mM Tris at pH 7.5, protease inhibitor and 1 mM DTT), and passed through an Insulin Syringe. Supernatants were clarified with a 10,000 g clearing spin for 10 min. and protein concentrations were determined. 1.8 mg protein was incubated with 15 ul of HA II beads (Covance, Calif.) for 2 h, washed 3× with lysis buffer and equilibrated in cleavage buffer (10 mM Tris at pH 7.5, 100 mM KCl, 2 mM MgCl2, Protease Inhibitor. 0.5 mM DTT). 0.1 nM 32P labeled target RNA was added and cleavage reactions quenched at specified times in gel loading buffer (Ambion, Tex.). Cleavage reactions were analyzed by denaturing PAGE and quantitated with Storm 850 Phosphorimager (Molecular Dynamics).

Example 13

Cell-Free Assay using Immunoprecipitated Ago2 (Post-load Assays)

To assess Ago2 activity in a cell-free assay, immunoprecipitates were prepared as above (Example 12) using cells treated with the Ago2 expression plasmid but not treated with synthetic oligoribonucleotides or siRNAs. Instead, immunoprecipitate equilibrated in cleavage buffer was incubated for 2 h with either the synthetic oligoribonucleotides or siRNAs. Immunoprecipitate was washed with cleavage buffer and 0.1 nM 32P labeled target RNA was added. Cleavage reactions were quenched and analyzed as above.

To assess Ago2 binding in a cell-free assay, immunoprecipitates were prepared as above for the cell-free activity assay except that 0.18 mg total protein was used. 0.1 nM 32P labeled antisense strand was incubated with the Ago2 immunoprecipitate in the presence of increasing concentrations of cold antisense strand or competitor nucleic acid construct for 2 h. The immunoprecipitate was washed in cleavage buffer to remove unbound nucleic acids. Binding reactions were stopped by the addition of scintillation cocktail and bound radioactivity analyzed in a scintillation counter. Bound radioactivity was plotted as a function of the cold competitor concentration and dissociation constants were determined from the non-linear regression fit of the data.

Example 14

Assays using Recombinant Ago2

The full length of hAgo2 was first sub-cloned into the pGEX-3× vector. The GST-Ago2 fusion DNA was further sub-cloned into the baculovirus shuttle vector pENTR2B.

Ago2 was expressed in Sf9 insect cells using BaculoDirect Baculovirus Expression System. Sf9 cells infected with high titer virus were harvested and the cells were gently lysed in PBS containing 0.5% NP-40, 1 mM DTT and proteases inhibitor and then centrifuged. The pellet was re-suspended and subject to sonication and re-centrifugation. Supernatants were GST affinity purified followed by HPLC purification. The purified GST-Ago2 protein yielded purities greater than 95%.

Ago2 activity assays and Ago2 binding assays using recombinant Ago2 were performed as above (Example 13) for immunoprecipitated Ago2. Binding and activity for various siRNAs were found to be similar using immunoprecipitated Ago2 and recombinant Ago2, despite the fact that recombinant Ago2 is not in association with other cellular factors, such as TRBP, which one might expect to influence binding and/or activity in the immunoprecipitated Ago2.

The invention claimed is;

1. A method of determining relative potency of a chemically-synthesized RNAi agent comprising:
   forming a first test sample comprising the chemically-synthesized RNAi agent and Ago, wherein the first test sample is not in a cell;
   forming a second test sample comprising an RNAi control agent and Ago2, wherein the second test sample is not in a cell; and
   measuring the Ago2 activity of the chemically-synthesized RNAi agent and the Ago2activity of the RNAi control agent, wherein the difference in the Ago2 activity of the chemically-synthesized RNAi agent and Ago2 activity of the control RNAi agent indicates potency of the chemically-synthesized RNAi agent relative to the control RNAi agent.

2. The method of claim 1, wherein the Ago2 is recombinant.

3. The method of claim 1, wherein the Ago2 is obtained by immunoprecipitation from a cell.

4. The method of claim 2, wherein the cell is made to over-express the Ago2 protein.

5. The method of claim 1, wherein the degree of binding is measured by measuring an amount of chemically-synthesized RNAi agent bound to the Ago2.

6. The method of claim 1, wherein the chemically-synthesized RNAi agent is an oligonucleotide.

7. The method of claim 6, wherein the oligonucleotide is from about 15 to about 27 nucleotides in length.

8. The method of claim 6, wherein the oligonucleotide comprises a complementary strand from about 15 to about 27 nucleotides in length.

9. The method of claim 6, wherein the oligonucleotide is an antisense oligoribonucleotide.

10. The method of claim 6, wherein the oligonucleotide comprises at least one sugar-modified nucleotide.

11. The method of claim 10, wherein the sugar-modified nucleotide is a 2' substituted nucleotide.

12. The method of claim 6, wherein the oligonucleotide comprises at least one modified internucleoside linkage.

13. The method of claim 12, wherein the modified internucleoside linkage is a phosphorothioate internucleoside linkage.

* * * * *

SEQUENCE LISTING

```
<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: Antisense Compound

<400> SEQUENCE: 1
ctgctggaat gtttccactt                                          20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gctgaccttt ttgcttctca                                          20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
tgcggtgggc tggcccagac                                          20

<210> SEQ ID NO 4
<211> LENGTH: 20
<212> TYPE: DNA
<213> ORGANISM: Artificial Sequence
<220> FEATURE:
<223> OTHER INFORMATION: Antisense Compound

<400> SEQUENCE: 4
gttaccattc tgtacaggta                                          20

<210> SEQ ID NO 5
<211> LENGTH: 19
<212> TYPE: DNA
<213> ORGANISM: Artificial Sequence
<220> FEATURE:
<223> OTHER INFORMATION: Antisense Compound

<400> SEQUENCE: 5
aagtaaggac cagagacaa                                           19

<210> SEQ ID NO 6
<211> LENGTH: 19
<212> TYPE: DNA
```

```
<213> ORGANISM: Artificial Sequence
<220> FEATURE:
<223> OTHER INFORMATION: Antisense Compound

<400> SEQUENCE: 6
ttgtctctgg tccttactt                                                19

<210> SEQ ID NO 7
<211> LENGTH: 19
<212> TYPE: DNA
<213> ORGANISM: Artificial Sequence
<220> FEATURE:
<223> OTHER INFORMATION: Antisense Compound

<400> SEQUENCE: 7
caacaaggat gaagtctat                                                19

<210> SEQ ID NO 8
<211> LENGTH: 19
<212> TYPE: DNA
<213> ORGANISM: Artificial Sequence
<220> FEATURE:
<223> OTHER INFORMATION: Antisense Compound

<400> SEQUENCE: 8
atagacttca tccttgttg                                                19

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ccagctacac tcagaccaac aga                                           23

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
gaaaacggag aatctaataa aatcaatgac                                    30

<210> SEQ ID NO 11
<211> LENGTH: 26
<212> TYPE: DNA
<213> ORGANISM: Artificial Sequence
<220> FEATURE:
<223> OTHER INFORMATION: Probe

<400> SEQUENCE: 11
cgtgacagcc agcatcgaac atgaga                                        26

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
attaaccttt tggtgtttga tgagtgt                                       27
```

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
gcgaggacat gatggacaaa tt                                              22

<210> SEQ ID NO 14
<211> LENGTH: 32
<212> TYPE: DNA
<213> ORGANISM: Artificial Sequence
<220> FEATURE:
<223> OTHER INFORMATION: Probe

<400> SEQUENCE: 14
atcttgcaat cctagaccac ccctatcgag aa                                   32

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
cagcccaccg caaagaat                                                   18

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tgccactccc aatctcaatg                                                 20

<210> SEQ ID NO 17
<211> LENGTH: 25
<212> TYPE: DNA
<213> ORGANISM: Artificial Sequence
<220> FEATURE:
<223> OTHER INFORMATION: Prober

<400> SEQUENCE: 17
caccatgacc tgtcgagtgg agcgt                                           25

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
gctgtgaata ttctcggttt gattt                                           25

<210> SEQ ID NO 19
<211> LENGTH: 22
<212> TYPE: DNA
<213> ORGANISM: Artificial Sequence
<220> FEATURE:
<223> OTHER INFORMATION: Primer -continued

```
<400> SEQUENCE: 19
ggaagctagt tttgggatcc aa                                              22

<210> SEQ ID NO 20
<211> LENGTH: 25
<212> TYPE: DNA
<213> ORGANISM: Artificial Sequence
<220> FEATURE:
<223> OTHER INFORMATION: Probe

<400> SEQUENCE: 20
tcctcccgag cacaacaagg agagg                                           25

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gccccaaatg tgaaagcatt                                                 20

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
ctaaagtggg cttttttgtga actct                                          25

<210> SEQ ID NO 23
<211> LENGTH: 19
<212> TYPE: DNA
<213> ORGANISM: Artificial Sequence
<220> FEATURE:
<223> OTHER INFORMATION: Probe

<400> SEQUENCE: 23
cctttaagag gcctaactc                                                  19

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
aatggctaag tgaagatgac aat                                             23

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
tgcacatatc attacaccag ttcgt                                           25

<210> SEQ ID NO 26
<211> LENGTH: 25
<212> TYPE: DNA
```

```
<213> ORGANISM: Artificial Sequence
<220> FEATURE:
<223> OTHER INFORMATION: Probe

<400> SEQUENCE: 26
agatgccgtg tttgatggct ccagc                                       25

<210> SEQ ID NO 27
<211> LENGTH: 19
<212> TYPE: RNA
<213> ORGANISM: Artificial Sequence
<220> FEATURE:
<223> OTHER INFORMATION: Antisense Compound

<400> SEQUENCE: 27
uugucucugg uccuuacuu                                              19

<210> SEQ ID NO 28
<211> LENGTH: 19
<212> TYPE: RNA
<213> ORGANISM: Artificial Sequence
<220> FEATURE:
<223> OTHER INFORMATION: Antisense Compound

<400> SEQUENCE: 28
auagacuuca uccuuguug                                              19

<210> SEQ ID NO 29
<211> LENGTH: 859
<212> TYPE: PRT
<213> ORGANISM: Homo Sapiens

<400> SEQUENCE: 29
```

Met Tyr Ser Gly Ala Gly Pro Ala Leu Ala Pro Ala Pro Pro Pro Pro
 1               5                  10                  15

Pro Ile Gln Gly Tyr Ala Phe Lys Pro Pro Pro Arg Pro Asp Phe Gly
                20                  25                  30

Thr Ser Gly Arg Thr Ile Lys Leu Gln Ala Asn Phe Phe Glu Met Asp
            35                  40                  45

Ile Pro Lys Ile Asp Ile Tyr His Tyr Glu Leu Asp Ile Lys Pro Glu
    50                  55                  60

Lys Cys Pro Arg Arg Val Asn Arg Glu Ile Val Glu His Met Val Gln
65                  70                  75                  80

His Phe Lys Thr Gln Ile Phe Gly Asp Arg Lys Pro Val Phe Asp Gly
                85                  90                  95

Arg Lys Asn Leu Tyr Thr Ala Met Pro Leu Pro Ile Gly Arg Asp Lys
            100                 105                 110

Val Glu Leu Glu Val Thr Leu Pro Gly Glu Gly Lys Asp Arg Ile Phe
        115                 120                 125

Lys Val Ser Ile Lys Trp Val Ser Cys Val Ser Leu Gln Ala Leu His
    130                 135                 140

Asp Ala Leu Ser Gly Arg Leu Pro Ser Val Pro Phe Glu Thr Ile Gln
145                 150                 155                 160

Ala Leu Asp Val Val Met Arg His Leu Pro Ser Met Arg Tyr Thr Pro
                165                 170                 175

Val Gly Arg Ser Phe Phe Thr Ala Ser Glu Gly Cys Ser Asn Pro Leu
            180                 185                 190

Gly Gly Gly Arg Glu Val Trp Phe Gly Phe His Gln Ser Val Arg Pro
        195                 200                 205

Ser Leu Trp Lys Met Met Leu Asn Ile Asp Val Ser Ala Thr Ala Phe

```
                210                 215                 220
Tyr Lys Ala Gln Pro Val Ile Glu Phe Val Cys Glu Val Leu Asp Phe
225                 230                 235                 240

Lys Ser Ile Glu Glu Gln Gln Lys Pro Leu Thr Asp Ser Gln Arg Val
            245                 250                 255

Lys Phe Thr Lys Glu Ile Lys Gly Leu Lys Val Glu Ile Thr His Cys
                260                 265                 270

Gly Gln Met Lys Arg Lys Tyr Arg Val Cys Asn Val Thr Arg Arg Pro
            275                 280                 285

Ala Ser His Gln Thr Phe Pro Leu Gln Gln Glu Ser Gly Gln Thr Val
    290                 295                 300

Glu Cys Thr Val Ala Gln Tyr Phe Lys Asp Arg His Lys Leu Val Leu
305                 310                 315                 320

Arg Tyr Pro His Leu Pro Cys Leu Gln Val Gly Gln Glu Gln Lys His
                325                 330                 335

Thr Tyr Leu Pro Leu Glu Val Cys Asn Ile Val Ala Gly Gln Arg Cys
            340                 345                 350

Ile Lys Lys Leu Thr Asp Asn Gln Thr Ser Thr Met Ile Arg Ala Thr
    355                 360                 365

Ala Arg Ser Ala Pro Asp Arg Gln Glu Glu Ile Ser Lys Leu Met Arg
370                 375                 380

Ser Ala Ser Phe Asn Thr Asp Pro Tyr Val Arg Glu Phe Gly Ile Met
385                 390                 395                 400

Val Lys Asp Glu Met Thr Asp Val Thr Gly Arg Val Leu Gln Pro Pro
                405                 410                 415

Ser Ile Leu Tyr Gly Gly Arg Asn Lys Ala Ile Ala Thr Pro Val Gln
            420                 425                 430

Gly Val Trp Asp Met Arg Asn Lys Gln Phe His Thr Gly Ile Glu Ile
            435                 440                 445

Lys Val Trp Ala Ile Ala Cys Phe Ala Pro Gln Arg Gln Cys Thr Glu
    450                 455                 460

Val His Leu Lys Ser Phe Thr Glu Gln Leu Arg Lys Ile Ser Arg Asp
465                 470                 475                 480

Ala Gly Met Pro Ile Gln Gly Gln Pro Cys Phe Cys Lys Tyr Ala Gln
                485                 490                 495

Gly Ala Asp Ser Val Glu Pro Met Phe Arg His Leu Lys Asn Thr Tyr
            500                 505                 510

Ala Gly Leu Gln Leu Val Val Val Ile Leu Pro Gly Lys Thr Pro Val
            515                 520                 525

Tyr Ala Glu Val Lys Arg Val Gly Asp Thr Val Leu Gly Met Ala Thr
    530                 535                 540

Gln Cys Val Gln Met Lys Asn Val Gln Arg Thr Thr Pro Gln Thr Leu
545                 550                 555                 560

Ser Asn Leu Cys Leu Lys Ile Asn Val Lys Leu Gly Gly Val Asn Asn
                565                 570                 575

Ile Leu Leu Pro Gln Gly Arg Pro Pro Val Phe Gln Gln Pro Val Ile
            580                 585                 590

Phe Leu Gly Ala Asp Val Thr His Pro Pro Ala Gly Asp Gly Lys Lys
            595                 600                 605

Pro Ser Ile Ala Ala Val Val Gly Ser Met Asp Ala His Pro Asn Arg
    610                 615                 620

Tyr Cys Ala Thr Val Arg Val Gln Gln His Arg Gln Glu Ile Ile Gln
625                 630                 635                 640
```

```
Asp Leu Ala Ala Met Val Arg Glu Leu Leu Ile Gln Phe Tyr Lys Ser
            645                 650             655

Thr Arg Phe Lys Pro Thr Arg Ile Ile Phe Tyr Arg Asp Gly Val Ser
        660                 665             670

Glu Gly Gln Phe Gln Gln Val Leu His His Glu Leu Leu Ala Ile Arg
        675                 680             685

Glu Ala Cys Ile Lys Leu Glu Lys Asp Tyr Gln Pro Gly Ile Thr Phe
    690                 695             700

Ile Val Val Gln Lys Arg His His Thr Arg Leu Phe Cys Thr Asp Lys
705                 710             715                 720

Asn Glu Arg Val Gly Lys Ser Gly Asn Ile Pro Ala Gly Thr Thr Val
                725             730                 735

Asp Thr Lys Ile Thr His Pro Thr Glu Phe Asp Phe Tyr Leu Cys Ser
            740             745             750

His Ala Gly Ile Gln Gly Thr Ser Arg Pro Ser His Tyr His Val Leu
            755             760             765

Trp Asp Asp Asn Arg Phe Ser Ser Asp Glu Leu Gln Ile Leu Thr Tyr
    770             775             780

Gln Leu Cys His Thr Tyr Val Arg Cys Thr Arg Ser Val Ser Ile Pro
785             790             795                 800

Ala Pro Ala Tyr Tyr Ala His Leu Val Ala Phe Arg Ala Arg Tyr His
            805             810             815

Leu Val Asp Lys Glu His Asp Ser Ala Glu Gly Ser His Thr Ser Gly
            820             825             830

Gln Ser Asn Gly Arg Asp His Gln Ala Leu Ala Lys Ala Val Gln Val
        835             840             845

His Gln Asp Thr Leu Arg Thr Met Tyr Phe Ala
850                 855
```